United States Patent [19]
Crea

[11] Patent Number: 5,961,973
[45] Date of Patent: Oct. 5, 1999

[54] PATHOGEN-TARGETED BIOCATALYSTS

[76] Inventor: Roberto Crea, 700 Occidental Ave., San Mateo, Calif. 94402

[21] Appl. No.: 08/558,269

[22] Filed: Nov. 13, 1995

Related U.S. Application Data

[63] Continuation-in-part of application No. 08/184,635, Jan. 18, 1994, abandoned, and a continuation-in-part of application No. 07/847,800, Mar. 6, 1992, abandoned.

[51] Int. Cl.⁶ .......................... A61K 39/42; A61K 38/43
[52] U.S. Cl. ................................ 424/133.1; 424/134.1; 424/94.3; 435/236; 435/69.7; 536/23.4
[58] Field of Search ............................ 424/133.1, 134.1, 424/94.3; 435/236, 69.7, 214, 226; 536/23.4

[56] References Cited

U.S. PATENT DOCUMENTS 4,671,958  6/1987  Rodwell et al. ........................ 424/85

FOREIGN PATENT DOCUMENTS

| 0 146 050 | 6/1985 | European Pat. Off. . |
| 0 187 658 | 7/1986 | European Pat. Off. . |
| WO 88/03559 | 5/1988 | WIPO . |
| WO 90/02338 | 3/1990 | WIPO . |
| WO 90/10015 | 9/1990 | WIPO . |

OTHER PUBLICATIONS

Berger et al., "CD4–Pseudomonas exotoxin hybrid protein blocks the spread of human immunodeficiency virus infection in vitro and its active against cels expressing the envelope glycoproteins from diverse primate immunodeficiency retroviruses" *Proceedings of the National Acedemy of Sciences*, vol. 86, No. 23, pp. 9539–9543 (Dec. 1989).

Capon et al., "Designing CD4 immunoadhesins for AIDS therapy" *Nature*, vol. 337, pp. 525–531 (Feb. 9, 1989).

Chaudhary et al., "Selective killing of HIV–infected cells by recombinant human CD4–Pseudomonas exotoxin hybrid protein" *Nature*, vol. 335, pp. 369–372, Sep. 22, (1988).

Clements et al., "The V3 Loop of the HIV–1 and HIV–2 Surface Glycoproteins Contain Proteolytic Cleavage Sites: A Possible Function in Viral Fusion?" *AIDS Research and Human Retroviruses*, vol. 7, No. 1, pp. 3–16 (1991).

Degen et al., "Characterization of the Complementary Deoxyribonulceic Acid and Gene Coding for Human Prothrombin" *Biochemistry*, vol. 22, pp. 2087–2097 (1983).

Pennica et al., Cloning and Expression of Human Tissue–type Plasminogen Activator of cDNA in *E. coli Nature*, vol. 201, pp. 214–221 (Jan. 20, 1983).

Poulin et al., "Several CD4 Domains Can Play a Role in Human Immunodeficiency Virus Infection of Cells" *Journal of Virology*, vol. 65, No. 9, pp. 4893–4901, Sep. 1991.

Schnee et al., "Construction and expression of recombinant antibody–targeted plasminogen activator" *Proceedings of the National Academy of Sciences*, vol. 84, pp. 6904–6903, Oct. 1987.

Till et al., "HIV–Infected Cells Are Killed by rCD4–Ricin A Chain" *Science*, vol. 242, pp. 1166–1168, Nov. 25, 1988.

Traunecker et al., "Highly efficient neutralization of HIV with recombinant CD4– immunoglobulin molecules" *Nature Letters to Nature*, vol. 339, pp. 68–71, May 4, 1989.

*Primary Examiner*—Charles L. Patterson, Jr.
*Attorney, Agent, or Firm*—Lahive & Cockfield, LLP; Giulio A. DeConti, Jr., Esq

[57] ABSTRACT

This invention pertains to biocatalysts that are specifically targeted to bind pathogens, such as viruses, and to degrade components of pathogens in order to abrogate their pathogenicity, and to methods of preventing or treating infection by pathogenic organisms. The biocatalysts comprise a binding agent which specifically binds a surface component of a pathogen, for instance the gp120 viral coat protein of the Human Immunodeficiency Virus, and a catalytic moiety which degrades a component of the pathogen so that its pathogenicity is abrogated. The binding agent and the catalytic moiety are linked by chemical linkers or genetic engineering techniques.

28 Claims, 13 Drawing Sheets

CD4 Construct

```
       BspHI
 AA TTC ATG AAG AAA GTA GTA CTT GGC AAG AAA GGC GAT ACA GTG GAG
       G TAC TTC TTT CAT CAT GAA CCG TTC TTT CCG CTA TGT CAC CTC

CTC ACG TGC ACA GCT AGC CAG AAG AAG AGC ATT CAA TTC CAC TGG AAG
GAG TGC ACG TGT CGA TCG GTC TTC TTC TCG TAA GTT AAG GTG ACC TTC

AAC TCC AAC CAG ATT AAG ATC CTT GGT AAC CAA GGT AGC TTC TTA ACT
TTG AGG TTG GTC TAA TTC TAG GAA CCA TTG GTT CCA TCG AAG AAT TGA

AAG GGC CCA TCC AAG CTT AAC GAT CGC GCT GAC TCT CGT CGT AGC CTT
TTC CCG GGT AGG TTC GAA TTG CTA GCG CGA CTG AGA GCA GCA TCG GAA

TGG GAC CAA GGT AAC TTT CCA CTG ATC ATC AAG AAT CTT AAG ATC GAA
ACC CTG GTT CCA TTG AAA GGT GAC TAG TAG TTC TTA GAA TTC TAG CTT

GAC TCT GAT ACG TAT ATC TGT GAA GTA GAG GAT CAG AAA GAG GAA GTT
CTG AGA CTA TGC ATA TAG ACA CTT CAT CTC CTA GTC TTT CTC CTT CAA
                                                                 <PstI
CAA CTG CTA GTA TTC GGC CTG ACT GCC AAC AGT GAC ACC CAT CTG CTG
GTT GAC GAT CAT AAG CCG GAC TGA CGG TTG TCA CTG TGG GTA GAC GAC

CAG GGC TAA TAG
GTC CCG ATT ATC CTA G
```

Fig. 1

CD4 /tPA fusion protein, part 1

<u>BspHI</u>
```
TC ATG AAG AAA GTA GTA CTT GGC AAG AAA GGC GAT ACA GTG GAG CTC ACG
   Met Lys Lys Val Val Leu Gly Lys Lys Gly Asp Thr Val Glu Leu Thr   16

TGC ACA GCT AGC CAG AAG AAG AGC ATT CAA TTC CAC TGG AAG AAC TCC
   Cys Thr Ala Ser Gln Lys Lys Ser Ile Gln Phe His Trp Lys Asn Ser   32

AAC CAG ATT AAG ATC CTT GGT AAC CAA GGT AGC TTC TTA ACT AAG GGC
   Asn Gln Ile Lys Ile Leu Gly Asn Gln Gly Ser Phe Leu Thr Lys Gly   48

CCA TCC AAG CTT AAC GAT CGC GCT GAC TCT CGT CGT AGC TTT TGG GAC
   Pro Ser Lys Leu Asn Asp Arg Ala Asp Ser Arg Arg Ser Leu Trp Asp   64

CAA GGT AAC TTT CCA CTG ATC ATC AAG AAT CTT AAG ATC GAA GAC TCT
   Gln Gly Asn Phe Pro Leu Ile Ile Lys Asn Leu Lys Ile Glu Asp Ser   80

GAT ACG TAT ATC TGT GAA GTA GAG GAT CAG AAA GAG GAA GTT CAA CTG
   Asp Thr Tyr Ile Cys Glu Val Glu Asp Gln Lys Glu Glu Val Gln Leu   96

CTA GTA TTC GGC CTG ACT GCC AAC AGT GAC ACC CAT CTG CTG CAT GGC
   Leu Val Phe Gly Leu Thr Ala Asn Ser Asp Thr His Leu Leu His Gly  112

CAG TCC CTG ACA CTG TCC ACC TGC GGC CTG AGA CAG TAC AGC CAG CCT
   Gln Ser Leu Thr Leu Ser Thr Cys Gly Leu Arg Gln Tyr Ser Gln Pro  128

CAG TTT CGC ATC AAA GGA GGG CTC TTC GCC GAC ATC GCC TCC CAC CCC
   Gln Phe Arg Ile Lys Gly Gly Leu Phe Ala Asp Ile Ala Ser His Pro  144

TGG CAG GCT GCC ATC TTT GCC AAG CAC AGG AGG TCG CCC GGA GAG CGG
   Trp Gln Ala Ala Ile Phe Ala Lys His Arg Arg Ser Pro Gly Glu Arg  160

TTC CTG TGC GGG GGC ATA CTC ATC AGC TCC TGC TGG ATT CTC TCT GCC
   Phe Leu Cys Gly Gly Ile Leu Ile Ser Ser Cys Trp Ile Leu Ser Ala  176

GCC CAC TGC TTC CAG GAG AGG TTT CCG CCC CAC CAC CTG ACG GTG ATC
   Ala His Cys Phe Gln Glu Arg Phe Pro Pro His His Leu Thr Val Ile  192

TTG GGC AGA ACA TAC CGG GTG GTC CCT GGC GAG GAG GAG CAG AAA TTT
   Leu Gly Arg Thr Tyr Arg Val Val Pro Gly Glu Glu Glu Gln Lys Phe  208

GAA GTC GAA AAA TAC ATT GTC CAT AAG GAA TTC GAT GAT GAC ACT TAC
   Glu Val Glu Lys Tyr Ile Val His Lys Glu Phe Asp Asp Asp Thr Tyr  224
```

Fig. 4A

CD4/tPA fusion protein, part 2

```
GAC AAT GAC ATT GCG CTG CTG CAG CTG AAA TCG GAT TCG TCC CGC TGT
Asp Asn Asp Ile Ala Leu Leu Gln Leu Lys Ser Asp Ser Ser Arg Cys  240

GCC CAG GAG AGC AGC GTG GTC CGC ACT GTG TGC CTT CCC CCG GCG GAC
Ala Gln Glu Ser Ser Val Val Arg Thr Val Cys Leu Pro Pro Ala Asp  256

CTG CAG CTG CCG GAC TGG ACG GAG TGT GAG CTC TCC GGC TAC GGC AAG
Leu Gln Leu Pro Asp Trp Thr Glu Cys Glu Leu Ser Gly Tyr Gly Lys  272

CAT GAG GCC TTG TCT CCT TTC TAT TCG GAG CGG CTG AAG GAG GCT CAT
His Glu Ala Leu Ser Pro Phe Tyr Ser Glu Arg Leu Lys Glu Ala His  288

GTC AGA CTG TAC CCA TCC AGC CGC TGC ACA TCA CAA CAT TTA CTT AAC
Val Arg Leu Tyr Pro Ser Ser Arg Cys Thr Ser Gln His Leu Leu Asn  304

AGA ACA GTC ACC GAC AAC ATG CTG TGT GCT GGA GAC ACT CGG AGC GGC
Arg Thr Val Thr Asp Asn Met Leu Cys Ala Gly Asp Thr Arg Ser Gly  320

GGG CCC CAG GCA AAC TTG CAC GAC GCC TGC CAG GGC GAT TCG GGA GGC
Gly Pro Gln Ala Asn Leu His Asp Ala Cys Gln Gly Asp Ser Gly Gly  336

CCC CTG GTG TGT CTG AAC GAT GGC CGC ATG ACT TTG GTG GGC ATC ATC
Pro Leu Val Cys Leu Asn Asp Gly Arg Met Thr Leu Val Gly Ile Ile  352

AGC TGG GGC CTG GGC TGT GGA CAG AAG GAT GTC CCG GGT GTG TAC ACA
Ser Trp Gly Leu Gly Cys Gly Gln Lys Asp Val Pro Gly Val Tyr Thr  368

AAG GTT ACC AAC TAC CTA GAC TGG ATT CGT GAC AAC ATG CGA CCG TGA
Lys Val Thr Asn Tyr Leu Asp Trp Ile Arg Asp Asn Met Arg Pro      383

TAG GGA TCC
    BamHI
```

Fig. 4B

5'Amplifier

NsiI            C-terminus of CD4

5'- ATG CAT  GGC CAG TCC CTG ACA CTG  ACC

Ile321+ of Thrombin

ATG GGT  AAG CTT  ATT GTG GAC GGC TCG  GAT -3'

3'Amplifier

SalI             C-terminus of Thrombin

5'- GTC GAC  CTA CTC TCC AAA CTG ATC AAT G -3'

Fig. 5

CD4/thrombin fusion protein, part 1

BspHI
```
TC ATG AAG AAA GTA GTA CTT GGC AAG AAA GGC GAT ACA GTG GAG CTC ACG
   Met Lys Lys Val Val Leu Gly Lys Lys Gly Asp Thr Val Glu Leu Thr  16

TGC ACA GCT AGC CAG AAG AAG AGC ATT CAA TTC CAC TGG AAG AAC TCC
   Cys Thr Ala Ser Gln Lys Lys Ser Ile Gln Phe His Trp Lys Asn Ser  32

AAC CAG ATT AAG ATC CTT GGT AAC CAA GGT AGC TTC TTA ACT AAG GGC
   Asn Gln Ile Lys Ile Leu Gly Asn Gln Gly Ser Phe Leu Thr Lys Gly  48

CCA TCC AAG CTT AAC GAT CGC GCT GAC TCT CGT CGT AGC CTT TGG GAC
   Pro Ser Lys Leu Asn Asp Arg Ala Asp Ser Arg Arg Ser Leu Trp Asp  64

CAA GGT AAC TTT CCA CTG ATC ATC AAG AAT CTT AAG ATC GAA GAC TCT
   Gln Gly Asn Phe Pro Leu Ile Ile Lys Asn Leu Lys Ile Glu Asp Ser  80

GAT ACG TAT ATC TGT GAA GTA GAG GAT CAG AAA GAG GAA GTT CAA CTG
   Asp Thr Tyr Ile Cys Glu Val Glu Asp Gln Lys Glu Glu Val Gln Leu  96

CTA GTA TTC GGC CTG ACT GCC AAC AGT GAC ACC CAT CTG CTG CAT GGC
   Leu Val Phe Gly Leu Thr Ala Asn Ser Asp Thr His Leu Leu His Gly 112

CAG TCC CTG ACA CTG ATT GTG GAG GGC TCG GAT GCA GAG ATC GGC ATG
   Gln Ser Leu Thr Leu Ile Val Glu Gly Ser Asp Ala Glu Ile Gly Met 128

TCA CCT TGG CAG GTG ATG CTT TTC CGG AAG AGT CCC CAG GAG CTG CTG
   Ser Pro Trp Gln Val Met Leu Phe Arg Lys Ser Pro Gln Glu Leu Leu 144

TGT GGG GCC AGC CTC ATC AGT GAC CGC TGG GTC CTC ACC GCC GCC CAC
   Cys Gly Ala Ser Leu Ile Ser Asp Arg Trp Val Leu Thr Ala Ala His 160

TGC CTC CTG TAC CCG CCC TGG GAC AAG AAC TTC ACC GAG AAT GAC CTT
   Cys Leu Leu Tyr Pro Pro Trp Asp Lys Asn Phe Thr Glu Asn Asp Leu 176

CTG GTG CGC ATT GGC AAG CAC TCC CGC ACC AGG TAC GAG CGA AAC ATT
   Leu Val Arg Ile Gly Lys His Ser Arg Thr Arg Tyr Glu Arg Asn Ile 192

GAA AAG ATA TCC ATG TTG GAA AAG ATC TAC ATC CAC CCC AGG TAC AAC
   Glu Lys Ile Ser Met Leu Glu Lys Ile Tyr Ile His Pro Arg Tyr Asn 208

TGG CGG GAG AAC CTG GAC CGG GAC ATT GCC CTG ATG AAG CTG AAG AAG
   Trp Arg Glu Asn Leu Asp Arg Asp Ile Ala Leu Met Lys Leu Lys Lys 224

CCT GTT GCC TTC AGT GAC TAC ATT CAC CCT GTG TGT CTG CCC GAC AGG
   Pro Val Ala Phe Ser Asp Tyr Ile His Pro Val Cys Leu Pro Asp Arg 240

GAG ACG GCA GCC AGC TTG CTC CAG GCT GGA TAC AAG GGG CGG GTG ACA
   Glu Thr Ala Ala Ser Leu Leu Gln Ala Gly Tyr Lys Gly Arg Val Thr 256
```

Fig. 6A

CD4/thrombin fusion protein, part 2

```
GGC TGG GGC AAC CTG AAG GAG ACG TGG ACA GCC AAC GTT GGT AAG GGG
Gly Trp Gly Asn Leu Lys Glu Thr Trp Thr Ala Asn Val Gly Lys Gly 272

CAG CCC AGT GTC CTG CAG GTG GTG AAC CTG CCC ATT GTG GAG CGG CCG
Gln Pro Ser Val Leu Gln Val Val Asn Leu Pro Ile Val Glu Arg Pro 288

GTC TGC AAG GAC TCC ACC CGG ATC CGC ATC ACT GAC AAC ATG TTC TGT
Val Cys Lys Asp Ser Thr Arg Ile Arg Ile Thr Asp Asn Met Phe Cys 304

GCT GGT TAC AAG CCT GAT GAA GGG AAA CGA GGG GAT GCC TGT GAA GGT
Ala Gly Tyr Lys Pro Asp Glu Gly Lys Arg Gly Asp Ala Cys Glu Gly 320

GAC AGT GGG GGA CCC TTT GTC ATG AAG AGC CCC TTT AAC AAC CGC TGG
Asp Ser Gly Gly Pro Phe Val Met Lys Ser Pro Phe Asn Asn Arg Trp 336

TAT CAA ATG GGC ATC GTC TCA TGG GGT GAA GGC TGT GAC CGG GAT GGG
Tyr Gln Met Gly Ile Val Ser Trp Gly Glu Gly Cys Asp Arg Asp Gly 352

AAA TAT GGC TTC TAC ACA CAT GTG TTC CGC CTG AAG AAG TGG ATA CAG
Lys Tyr Gly Phe Tyr Thr His Val Phe Arg Leu Lys Lys Trp Ile Gln 368

_____ <SalI
AAG GTC ATT GAT CAG TTT GGA GAG TAG GTC GAC
Lys Val Ile Asp Gln Phe Gly Glu  *                              376
```

Fig. 6B

1 - 8.0 µM, 2 - 4.0 µM, 3 - 2.0 µM, 4 - 1.0 µM, 5 - 0.5 µM
6 - 0.2 µM, 7 - 0.1 µM, 8 - 0.02 µM, 9 - none

PATHOGEN-TARGETED BIOCATALYSTS

RELATED APPLICATIONS

This application is a continuation-in-part of U.S. Ser. No. 08/184,635 filed Jan. 18, 1994 now abandoned and U.S. Ser. No. 07/847,800 filed Mar. 6, 1992, now abandoned each of which is entitled "Pathogen-Targeted Biocatalysts". The teachings of U.S. Ser. Nos. 08/184,635 and 07/847,800 are incorporated herein by reference.

BACKGROUND OF THE INVENTION

Pathogenic organisms, including viruses, may be divided into different classes on the basis of their fate after being phagocytized. For instance, organisms that are promptly destroyed when phagocytized (i.e., S. pneumoniae, S. pyogenes) behave as extracellular parasites, damaging tissues only so long as they remain outside phagocytic cells.

Pathogens that function as extracellular parasites owe their virulence to antiphagocytic surface components. Most pathogenic bacteria for example, maintain capsules comprising high-molecular-weight polysaccharides. The relation between capsules, phagocytosis and virulence is clearly exemplified by S. pneumoniae. A fully encapsulated S (smooth) strain is found to resist phagocytosis (in the absence of antibodies) and is highly virulent for mice, whereas its nonencapsulated R (rough) mutant is readily phagocytized and is essentially avirulent. However, enzymatic removal of the capsular polysaccharide, or combination with antibody, renders the S organisms both nonpathogenic and susceptible to phagocytosis.

In contrast to extracellular parasites, there are two classes of intracellular parasites, both of which can multiply within phagocytic cells. One class of these intracellular pathogens comprise the obligate intracellular parasites (i.e., rickettsiae, chlamydiae). For these organisms, which include viruses, subtle differences in the cell surface receptors essential for their uptake may be important in resistance.

Many pathogens, whether intracellular or extracellular, are organotropic. That is, they are highly selective in regard to the tissue or cell-type that they infect or invade. One determinant of tissue tropism is the presence of surface macromolecules on the pathogen that promote adherence to specific receptors on one host cell-type but not on others. For instance, the role of specific bacterial adherence is now increasingly recognized in the selective colonization of host tissue or cell-types. For many obligate intracellular parasites, the molecules responsible for organotropic adherence are also crucial to the internalization of the pathogen.

Blocking this cell-specific interaction aids in the destruction of pathogenicity. For instance, antibodies to pathogen surface constituents promote immunity not only by opsonization but also by covering antigens involved in adherence. Moreover, in body secretions, secreted glycoproteins closely related to cell surface components may play a role in host defense by competing with fixed receptors and thus preventing adsorption of adherent pathogens.

Viruses, which are noncellular in nature, are vastly less complex than prokaryotic or eukaryotic cellular systems. Although as a group they are extremely heterogeneous, all viruses share certain basic properties. All viruses are obligate intracellular parasites; i.e., they cannot reproduce unless present within some host cell. Outside of the host cell, the virus exists as a particle, or virion, in which its genetic material is enclosed within a capsid shell comprising protein subunits, and in some instances, a membranous envelope as well.

Viruses have been demonstrated to exhibit cell-specific tropism in that a given virus will infect only certain cell-types. The host cell range of the virus is determined by the specificity of attachment to the cells, which depends on properties of both the virion's capsid and specific receptors on the cell surface. The influenza viruses, for example, have as part of their capsid structure the hemagglutinin protein which facilitates the binding of the virus to receptors present on host cells. These limitations disappear when transfection occurs, i.e., when infection is carried out by the naked viral nucleic acid, whose entry does not depend on virus-specific receptors.

CD4, a surface glycoprotein found primarily on a subset of T lymphocytes, is a receptor for both the class II major histocompatability complex (MHC) antigens and the human immunodeficiency viruses (HIV). The tropism of the HIV virus for CD4+ cells is governed through the direct binding and high affinity interactions between virion-associated gp120 protein and CD4 (McDougal et al. (1986) *Science* 231:382 and Lasky et al. (1987) *Cell* 50:975). In addition, cells expressing the envelope protein fuse with CD4-bearing cells in culture (Lipson et al. (1986) *Nature* 323:725 and Sodroski et al. (1986) *Nature* 322:470), resulting in the formation of multinucleate syncytia.

The most amino-terminal immunoglobulin-like domain of CD4 is sufficient to bind gp120, although the second domain has also been shown to contribute to binding (Traunecker et al. (1988) *Nature* 331:84; Berger et al. (1988) *PNAS* 85:2357; Richardson et al. (1988) *PNAS* 85:6102 and Clayton et al. (1988) *Nature* 335:363). Additionally, studies of carbohydrate-mediated interactions of the envelope glycoprotein, gp120, have presented evidence that binding to cell surfaces may also involve the carbohydrate moieties of gp120 (Larkin et al., 1989 *AIDS* 3:793). Antiviral therapies directed towards abrogating proliferation of the HIV virus have been directed to specifically inhibiting interactions between CD4 and gp120. Strategies have included antibodies directed against various epitopes on gp120, facilitated for instance by immunization with immunogenic peptides resembling portions of gp120 or administration of anti-gp120 monoclonal antibodies. Both native and recombinant gp120 elicit antibodies that are capable of neutralizing HIV in cell culture (Robey et al. (1986) *PNAS* 83:9709; Laskey et al. (1986) *Science* 233:209 and Putney et al. (1986) *Science* 234:1392). These antibodies however are generally neutralizing only to the variant from which the immunizing gp120 was derived.

Studies in humans and mice have revealed a small region of gp120, termed the V3 loop or principal neutralizing determinant, comprising about 35 residues between two invariant, disulfide-crosslinked cysteines (Cys-303 to Cys-338: HIV-1 nomenclature of Takahashi et al. (1992) Science 255:333), that evokes the major neutralizing antibodies to the virus (Palker et al. (1988) *PNAS* 85:1932; Rusche et al. (1988) *PNAS* 85:3198 and Goudsmit et al. (1988) *PNAS* 85:4478). While this same region is one of the most variable in sequence among different clonal isolates (Takahashi et al. (1992) *Science* 255:333), analysis of the amino acid sequences of this domain revealed conservation to better than 80-percent of the amino acids in 9 out of 14 positions in the central portion of the V3 loop, suggesting that there are constraints on the V3 loop variability (LaRosa et al. (1990) *Science* 249:932). These results suggest that HIV vaccine immunogens chosen because of their similarity to the consensus V3 loop sequence and structure are likely to induce antibodies that neutralize a majority of HIV isolates.

Soluble forms of CD4 have been shown to be capable of inhibiting the interaction between HIV gp120 and CD4+ cells, presumably by binding and masking gp120 on the surface of the virus or infected cell (Traunecker et al. (1989) *Nature* 339:68; Fisher et al. (1988) *Nature* 331:76; Chao et al. (1989) *JBC* 264:5812 and Capon et al. (1989) *Nature* 337:525). Compounds such as Dextran sulphate and aurintricarboxylic acid, which act to bind CD4 and thereby inhibit gp120 binding, have been explored for use as HIV prophylaxis (Schols et al. (1989) *PNAS* 86:3322 and Lederman et al. (1989) *J Immunol.* 143:1149). Recently, N-carboxymethoxy-carbonyl-prolyl-phenylalanyl benzyl esters have been shown to irreversibly denature gp120 in such a manner as to abrogate binding to CD4 and inhibit HIV-1 infection (Finberg et al. (1990) *Science* 249:287).

The use of toxins targeted to HIV infected cells has also been explored. For instance, the gp120-binding domain of CD4 has been linked to the Pseudomonas exotoxin A molecule such that cells expressing the HIV gp120 molecule are selectively destroyed (Chaudhary et al. (1988) *Nature* 335:369). Immunotoxins comprising human monoclonal antibodies specific for epitopes of the envelope proteins of HIV, gp120 or gp41, conjugated to toxins such as ricin A chain or diphtheria toxin, have been employed to specifically kill HIV infected cells (Till et al. (1989) *PNAS* 86:1987). Alternatively, pokeweed mitogen, targeted to CD4+ cells has been shown to efficiently block HIV protein synthesis and also strongly inhibit HIV production in activated CD4+ T cells from infected patients (Zarling et al. (1990) *Nature* 347:92).

It has recently been reported that located close to the crown of the V3-type specific neutralization loop of the HIV-1 virus, are several potential sites that are susceptible to proteolytic cleavage by enzymes of trypsin-like or chymotrypsin-like specificity, or by aspartic proteases. (See for example, Clements et al., 1991, *AIDS Research and Human Retroviruses* 7:3; Hattori et al., 1989, *FEBS Letters* 248:48; Kioto et al., 1989, *INT Immunol.* 1:613; Stephens et al., 1990, *Nature* 343:219., incorporated by reference herein.)

SUMMARY OF THE INVENTION

This invention pertains to biocatalysts that are specifically targeted to bind pathogens and to degrade components of pathogens in order to abrogate their pathogenicity, and to methods of preventing or treating infection by pathogenic organisms. The biocatalysts comprise a binding agent which specifically binds a surface component of a pathogen and a catalytic moiety which degrades a component of the pathogen so that its pathogenicity is abrogated. The binding agent and the catalytic moiety are linked by chemical or genetic engineering techniques.

The binding agent is typically an antibody, a receptor or an analogue of either of these which is specific for the targeted surface component. Alternatively, the binding agent can be a polyanionic or polycationic molecule able to bind by ionic interactions to a charged determinant on a surface component of the pathogen.

The catalytic moiety is an enzyme or catalytic antibody which degrades or substantially alters a component of the pathogen sufficiently to abrogate pathogenicity. Examples of enzymes include proteases, glycosidases, lipases and other hydrolases. The component of the pathogen targeted for degradation by the catalytic moiety can be the same or different from the component targeted for binding by the binding agent. For bacterium, the targeted component can be a capsular constituent. For a virus, the surface component can be an envelope protein or glycoprotein, preferably one which interacts with the cellular receptor for the virus and is involved in the mechanism of infection. An example is the gp120 envelope glycoprotein of HIV-1. To target this component, the binding agent can be an antibody specific for gp120, or a portion of the CD4 receptor able to bind gp120.

The biocatalyst of this invention can be used to prevent or treat infection by pathogenic organisms. The biocatalyst is administered to the host organism in a physiologically acceptable vehicle in amounts sufficient to abrogate pathogenicity.

BRIEF DESCRIPTION OF THE DRAWINGS

FIG. 1 shows the double stranded nucleic acid sequence (SEQ ID No. 1) for a CD4 gene fragment.

FIGS. 4A and 4B show the nucleic acid sequence (SEQ ID No. 5) of a CD4/tPA fusion gene and the corresponding amino acid sequence (SEQ ID No. 6).

FIG. 5 shows 5' (SEQ ID No. 7) and 3' (SEQ ID No. 8) amplimers for PCR amplifying a catalytic domain containing fragment of thrombin.

FIGS. 6A and 6B show the nucleic acid sequence (SEQ ID No. 9) of a CD4/Thrombin fusion gene and the corresponding amino acid sequence (SEQ ID No. 10).

(FIG. 8) HIV-1RF ($2.7 \times 10^{10}$ virus/ml) was incubated with a range of concentrations (0-8.0 $\mu$M) of UK for 60 minutes and then incubated with MT-2 cells ($2 \times 10^5$/ml) for 5 days. (FIG. 9) HIV-1RF ($2.7 \times 10^{11}$ virus/ml) was incubated with 2 $\mu$M UK for 0–60 minutes and then incubated with MT-2 cells for 5 days. No additional enzymes were added during the virus-cell incubation in either series of experiments. Surviving cells were again measured by the MTT assay. The percent inhibition of infectivity was calculated from the control value. 1: 8.0 $\mu$M UK; 2: 4.0 $\mu$M; 3: 2.0 $\mu$M; 4: 1.0 $\mu$M; 5: 0.5 $\mu$M; 6: 0.2 $\mu$M; 7: 0.1 ($2.7 \times 10^{10}$ virus/ml); 8: 0.02 $\mu$M; 9: none.

DETAILED DESCRIPTION OF THE INVENTION

Figure 2:
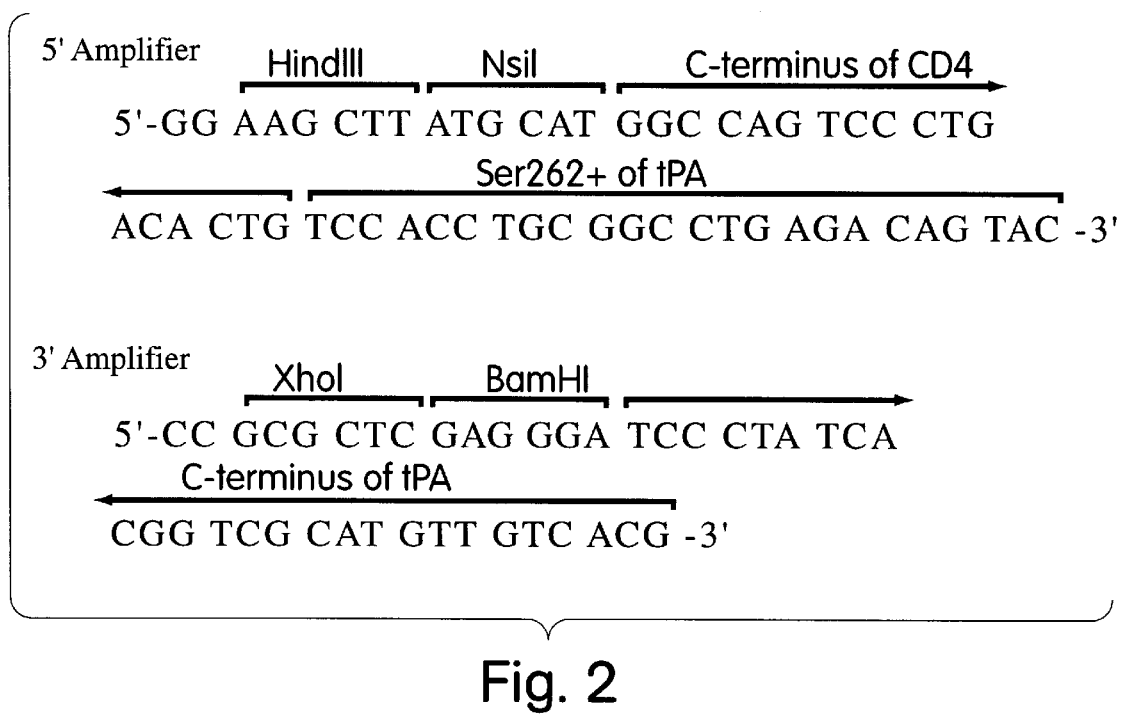
FIG. 2 shows 5' (SEQ ID No.3) and 3' (SEQ ID No.4) amplimers for PCR amplifying a catalytic domain fragment of tissue plasminogen activator (tPA).

Surface components of pathogens can play a major role in the survival of the pathogen, and therefor in its pathogenicity to a host. For instance, a given surface component can be crucial to the interaction of the pathogen with a host cell or tissue and is thus a critical component of the tissue-tropism of the pathogen. For intracellular pathogens, the surface component may be required for entry into the cell, while in the case of extracellular pathogens, particular surface components may be vital to the evasion of phagocytosis. Other surface components, such as the proteins, lipids and polysaccharides making up cellular walls, nutrient receptors including endocytic and pinocytic components, and chemotaxic receptors, can also be critical to the survival of the pathogen. The present invention provides a biocatalyst, directed against a surface component of a pathogen necessary for pathogenicity, such that action upon this component by the catalytic moiety destroys the functional integrity of this molecule and thereby disrupts pathogenicity.

A distinct advantage of the biocatalyst of the present invention comes from the catalytic nature of the molecule's action on a pathogen. As stated above, interaction between surface components of pathogens and host cells have been implicated in pathogenicity. Disruption of these interactions has generally been accomplished by way of molecules which bind and mask essential determinants of at least one of the involved surface components. The typical masking molecule, such as a soluble receptor, requires a large number of molecules in circulation in order to effectively neutralize the pathogen, as the masking molecule acts stoichiometrically rather than catalytically. The pathogen-targeted biocatalysts of this invention direct a catalytic moiety to a surface component of the pathogen. The surface component is degraded and normal pathogen/cellular interactions are disrupted, thereby abrogating pathogenicity. The effectiveness of the biocatalyst is enhanced by the fact that the molecule, upon degradation of the surface component, is not "consumed" by the reaction.

Most current regimens of therapy directed to disrupting pathogenicity by affecting the function of a surface component of a pathogen, act by masking the bound component.

I. The Biocatalyst

The pathogen-targeted biocatalysts of this invention comprise a binding agent that specifically recognizes and binds a surface component of the pathogen, and a catalytic moiety which degrades the surface component or some other component located proximal thereto-such that the functional integrity of the surface component is destroyed and pathogenicity is disrupted. For instance, interactions between surface components of the pathogen and host cell can be disrupted, thereby abrogating pathogenicity.

A. The Binding Agent

The binding agent, which directs the molecule to the surface component of the pathogen, is preferably specific for determinants of the pathogen, with substantially less binding affinity for host components. The association constant of the binding agent can be selected or tailored to provide sufficient selectivity, but low enough that the biocatalyst is "turned over" at an acceptable rate. The binding agent can comprise an antibody or binding fragment thereof, including but not limited to: individual chain antibodies of either heavy or light chain origin; the variable region or a portion thereof from a light ($V_L$) or heavy chain ($V_H$) or a fragment containing both; an F(ab), F(ab)$_2$, F$_V$, sF$_V$ (single chain antibody) or substantially similar antibody fragments; a heavy/light chain (HL) pair.

In addition, the antibody or binding fragment can be a chimeric antibody, wherein one part of the molecule is of human origin and the rest originates from a different species. For instance, the variable regions of a murine monoclonal antibody directed against the surface component of a pathogen can be engineered into both human heavy and light chains. More preferable is the engineering of the mouse complementarity-determining regions (CDRs) or hypervariable regions into the variable regions of human heavy and light chains. The advantage to a chimeric antibody of this nature is in reduced immunogenicity due to a reduced set of non-self antigens. Methods for constructing antibodies of this type are described in Reichmann et al. (1988) *Nature* 332:323; Verhoeyen et al. (1988) *Science* 329:1534; Sun et al. (1987) *PNAS* 84:214; and Jones et al. (1986) *Nature* 321:522, and incorporated by reference herein.

The binding agent can also be a receptor or a portion of a receptor sufficient to specifically bind the surface component of the pathogen. The receptor can be a single peptide chain or multiple peptide chains held together by endogenous disulfide bonds or exogenous chemical linkages. The receptor can be cleaved from the surface of a cell and purified. Alternatively, the sequence can be cloned and expressed in an exogenous system for purification.

In some instances, it will be appropriate to use molecules that exploit ionic interactions with determinants of the surface component that have a localized charge. Polyanionic or polycatonic binding agents such as oligonucleotides, heparin, lentinan and similar polysaccharide chains, polyamino peptides such as poly-aspartate, poly-glutamate, poly-lysine and poly-arginine, or other binding agents which maintain a number of either negative or positive charges over their structure at physiological pH's, can be used to specifically bind the protein component. Likewise, binding agents which exploit hydrophobic interactions can be utilized to target the biocatalyst.

B. The Catalytic Moiety

The catalytic moiety of the pathogen-targeted biocatalyst can be a protease, a glycosidase, a lipase, or other hydrolases, or other enzymatic activity, including isomerases, transferases (including kinases), lyases and oxidoreductases, capable of degrading a surface component of the pathogen. In order to destroy pathogenicity, the degradation can, in the case of obligate intracellular parasites, destroy the ability of the pathogen to bind surface components of the host cell, or alternatively, destroy some other surface component essential for the survival of the parasite. For extracellular parasites, degradation can facilitate phagocytosis or disrupt some other component essential for survival.

Examples of proteases, or catalytically active fragments thereof, that can be utilized to this end include serine proteases, cysteine proteases, aspartate or acid proteases, metalloproteases or any other protease capable of cleaving the amide backbone of the surface component in order to destroy the binding determinant necessary for productive interaction with a host cell or tissue or in the evasion of phagocytosis.

Glycosidases, defined here as glycolytic enzymes which can alter the carbohydrate structure of the surface component of the pathogen, are useful in instances such as when carbohydrate-mediated interaction of the surface component of the pathogen with host cells is important to pathogenicity. Lysozyme is an example of a hydrolytic enzyme directed to polysaccharides, and has been demonstrated to be bacteriolytic due to the enzyme's ability to hydrolyze glycosidic linkages in the bacterial cell wall. Likewise, lipases can be employed to alter the membrane structure of the pathogen in order to abrogate binding, facilitate phagocytosis, or disrupt viability of the pathogen.

Naturally occurring enzymes can be purified, or when possible, recombinant enzymes can be expressed and purified. In the instance of recombinant proteins, it can be useful to add mutations which will facilitate easy purification or direct the derivatization with chemical linking groups. For example, the addition of a free sulfhydryl group by way of site-directed mutagenesis, such as the introduction of a cysteine, can allow purification by mercury-derivatized columns to be carried out, as well as provide a reaction site for a chemical linking agent.

The protein can be obtained whole, or as a fragment, so long as a suitable catalytic activity is associated with the purified protein. In some instances, the enzyme may be isolated as the pro-form, requiring further modification such as enzymatic cleavage to provide the active, mature form of the enzyme.

Proteases that are useful as catalytic moieties in the present invention include: serine proteases such as chymotrypsin, trypsin, elastase, plasmin, tissue-type plasminogen activator (t-PA), urokinase (UK), single-chain urokinase (scu-PA), thrombin, kallikrein, acrosin, cathepsin G, coagulation factors VIIa, IXa and XIa; cysteine proteases such as cathepsin B, papain, ficin, chymopapain, clostripain and cathepsin L; and acid proteases such as the pepsins, chymosin and cathepsin D.

Many purified serine proteases are commercially available, including: leukocyte elastase from human leukocytes (Sigma Catalog No. E1508); pancreatic elastase from human sputum (Sigma Catalog No. E1633); plasmin from human plasma (Sigma Catalog No. P4895); single-chain t-PA from human melanoma cell cultures (Sigma Catalog No. T7776); recombinant two-chain t-PA (Sigma Catalog No. T4654); urokinase from human kidney cells (Sigma Catalog No. U5004); urokinase from human urine (Sigma Catalog No. U6876); Trypsin (Sigma Catalog No. T8003); and alpha-Chymotrypsin (Sigma Catalog No. C7762).

Other useful enzymes include: pancreatic lipase; lipoprotein lipases; monoglyceride lipase; sphingosylglucopyranoside; sphingomyelinase; phosphoinosisides; phospholipases; peptidases such as carboxypeptidases, aminopeptidases and dipeptidases; glucosidases; glucanases; galactosidases; mannosidases; amylases and dextrinases.

In addition, the catalytic moiety can be a catalytic antibody. Because antibodies can be generated that selectively bind almost any molecule of interest, this technology offers the potential to tailor-make highly selective catalysts. Methods for making catalytic antibodies are disclosed by Lerner et al. (1991) *Science* 252:659; Benkovic et al. (1990) *Science* 250:1135; Tramontano et al. (1986) *Science* 234:1566, all of which are incorporated by reference herein. Alternatively, tailoring of an antibody to create a catalytic antibody can be carried out by methods such as walk-through mutagenesis (see PCT application PCT/US91/02362, incorporated by reference herein).

II. Methods of Making the Biocatalysts

The catalytic moiety can be linked to the binding agent in a number of ways including by chemical coupling means, or by genetic engineering.

A. Chemical Coupling Agents

There are a large number of chemical cross-linking agents that are known to those skilled in the art. For the present invention, the preferred cross-linking agents are heterobifunctional cross-linkers, which can be used to link proteins in a stepwise manner. Heterobifunctional cross-linkers provide the ability to design more specific coupling methods for conjugating proteins, thereby reducing the occurrences of unwanted side reactions such as homo-protein polymers. A wide variety of heterobifunctional cross-linkers are known in the art. These include: succinimidyl 4-(N-maleimidomethyl) cyclohexane-1-carboxylate (SMCC), m-Maleimidobenzoyl-N- hydroxysuccinimide ester (MBS); N-succinimidyl (4-iodoacetyl) aminobenzoate (SIAB), succinimidyl 4-(p-maleimidophenyl) butyrate (SMPB), 1-ethyl-3-(3-dimethylaminopropyl)carbodiimide hydrochloride (EDC); 4-succinimidyloxycarbonyl-a-methyl-a-(2-pyridyldithio)-tolune (SMPT), N-succinimidyl 3-(2-pyridyldithio)propionate (SPDP), succinimidyl 6-[3-(2-pyridyldithio)propionate]hexanoate (LC-SPDP). Those cross-linking agents having N-hydroxysuccinimide moieties can be obtained as the N-hydroxysulfosuccinimide analogs, which generally have greater water solubility. In addition, those cross-linking agents having disulfide bridges within the linking chain can be synthesized instead as the alkyl derivatives so as to reduce the amount of linker cleavage in vivo.

In addition to the heterobifunctional cross-linkers, there exists a number of other cross-linking agents including homobifunctional and photoreactive cross-linkers. Disuccinimidyl suberate (DSS), bismaleimidohexane (BMH) and dimethylpimelimidate-2 HCl (DMP) are examples of useful homobifunctional cross-linking agents, and bis-[β-(4-azidosalicylamido)ethyl]disulfide (BASED) and N-succinimidyl-6(4'-azido-2'-nitrophenylamino)hexanoate (SANPAH) are examples of useful photoreactive cross-linkers for use in this invention. For a recent review of protein coupling techniques, see Means et al. (1990) *Bioconjugate Chemistry* 1:2–12, incorporated by reference herein. One particularly useful class of heterobifunctional cross-linkers, included above, contain the primary amine reactive group, N-hydroxysuccinimide (NHS), or its water soluble analog N-hydroxysulfosuccinimide (sulfo-NHS). Primary amines (lysine epsilon groups) at alkaline pH's are unprotonated and react by nucleophilic attack on NHS or sulfo-NHS esters. This reaction results in the formation of an amide bond, and release of NHS or sulfo-NHS as a by-product.

Another reactive group useful as part of a heterobifunctional cross-linker is a thiol reactive group. Common thiol reactive groups include maleimides, halogens, and pyridyl disulfides. Maleimides react specifically with free sulfhydryls (cysteine residues) in minutes, under slightly acidic to neutral (pH 6.5–7.5) conditions. Halogens (iodoacetyl functions) react with —SH groups at physiological pH's. Both of these reactive groups result in the formation of stable thioether bonds.

The third component of the heterobifunctional cross-linker is the spacer arm or bridge. The bridge is the structure that connects the two reactive ends. The most apparent attribute of the bridge is its effect on steric hindrance. In some instances, a longer bridge can more easily span the distance necessary to link two complex biomolecules. For instance, SMPB has a span of 14.5 angstroms.

Preparing protein-protein conjugates using heterobifunctional reagents is a two-step process involving the amine reaction and the sulfhydryl reaction. For the first step, the amine reaction, the protein chosen should contain a primary amine. This can be lysine epsilon amines or a primary alpha amine found at the N-terminus of most proteins. The protein should not contain free sulfhydryl groups. In cases where both proteins to be conjugated contain free sulfhydryl groups, one protein can be modified so that all sulfhydryls are blocked using for instance, N-ethylmaleimide (see Partis et al. (1983) J. Pro. Chem. 2:263, incorporated by reference herein). Ellman's Reagent can be used to calculate the quantity of sulfhydryls in a particular protein (see for example Ellman et al. (1958) Arch. Biochem. Biophys. 74:443 and Riddles et al. (1979) Anal. Biochem. 94:75, incorporated by reference herein).

The reaction buffer should be free of extraneous amines and sulfhydryls. The pH of the reaction buffer should be 7.0–7.5. This pH range prevents maleimide groups from reacting with amines, preserving the maleimide group for the second reaction with sulfhydryls.

The NHS-ester containing cross-linkers have limited water solubility. They should be dissolved in a minimal amount of organic solvent (DMF or DMSO) before introducing the cross-linker into the reaction mixture. The cross-linker/solvent forms an emulsion which will allow the reaction to occur.

The sulfo-NHS ester analogs are more water soluble, and can be added directly to the reaction buffer. Buffers of high ionic strength should be avoided, as they have a tendency to "salt out" the sulfo-NHS esters. To avoid loss of reactivity due to hydrolysis, the cross-linker is added to the reaction mixture immediately after dissolving the protein solution.

The reactions can be more efficient in concentrated protein solutions. The more alkaline the pH of the reaction mixture, the faster the rate of reaction. The rate of hydrolysis of the NHS and sulfo-NHS esters will also increase with increasing pH. Higher temperatures will increase the reaction rates for both hydrolysis and acylation.

Once the reaction is completed, the first protein is now activated, with a sulfhydryl reactive moiety. The activated protein may be isolated from the reaction mixture by simple gel filtration or dialysis. To carry out the second step of the cross-linking, the sulfhydryl reaction, the protein chosen for reaction with maleimides, activated halogens, or pyridyl disulfides must contain a free sulfhydryl, usually from a cysteine residue. Free sulfhydryls can be generated by reduction of protein disulfides. Alternatively, a primary amine may be modified with Traut's Reagent to add a sulfhydryl (Blattler et al. (1985) Biochem 24:1517, incorporated by reference herein). Again, Ellman's Reagent can be used to calculate the number of sulfhydryls available in protein.

In all cases, the buffer should be degassed to prevent oxidation of sulfhydryl groups. EDTA may be added to chelate any oxidizing metals that may be present in the buffer. Buffers should be free of any sulfhydryl containing compounds.

Maleimides react specifically with —SH groups at slightly acidic to neutral pH ranges (6.5–7.5). A neutral pH is sufficient for reactions involving halogens and pyridyl disulfides. Under these conditions, maleimides generally react with —SH groups within a matter of minutes. Longer reaction times are required for halogens and pyridyl disulfides.

The first sulfhydryl reactive-protein prepared in the amine reaction step is mixed with the sulfhydryl-containing protein under the appropriate buffer conditions. The protein-protein conjugates can be isolated from the reaction mixture by methods such as gel filtration or by dialysis.

B. Recombinant Fusion Proteins

The biocatalyst of this invention can be constructed as a fusion protein, containing the catalytic moiety and the binding agent as one contiguous polypeptide chain. In preparing the fusion protein, a fusion gene is constructed comprising DNA encoding the sequences for the binding agent, the catalytic moiety, and optionally, a peptide linker sequence to span the two fragments. To make this fusion protein, an entire enzyme can be cloned and expressed as part of the protein, or alternatively, a suitable fragment containing the catalytic moiety can be used. Likewise, the entire cloned coding sequence of a binding agent such as a receptor or antibody, or alternatively, a fragment of the molecule capable of binding the surface component of the pathogen can be used. The use of recombinant DNA techniques to create a fusion gene, with the translational product being the desired fusion protein, is well known in the art. Both the coding sequence of a gene and its regulatory regions can be redesigned to change the functional properties of the protein product, the amount of protein made, or the cell type in which the protein is produced. The coding sequence of a gene can be extensively altered—for example, by fusing part of it to the coding sequence of a different gene to produce a novel hybrid gene that encodes a fusion protein. Examples of methods for producing fusion proteins are described in PCT applications PCT/US87/02968, PCT/US89/03587 and PCT/US90/07335, as well as Traunecker et al. (1989) *Nature* 339:68, incorporated by reference herein.

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling in of cohesive ends as appropriate, alkaline phosphatase treatment to avoid undesirable joining, and enzymatic ligation. Alternatively, the fusion gene can be synthesized by conventional techniques including automated DNA synthesizers.

To express the fusion protein molecule, it may be desirable to include transcriptional and translational regulatory elements and other non-coding sequences to the fusion gene construct. For instance, regulatory elements including constituitive and inducible promoters, enhancers or inhibitors can be incorporated.

These regulatory control sequences include, for example, the lac system, the β-lactamase system, the TAC system, the TRC system, the major operator and promoter regions of phage lambda, the promoters of the yeast a-mating factors, the SV40 early promoter, adenovirus late promoter, the GC box, the 72 Base pair repeats, the TATA box, the TAR transactivation sequence, the Shine-Dalgarno sequence, the IPTG inducible promoter, and other sequences known to control prokaryotic and eukaryotic cells or their viruses and various combinations thereof.

For expression is eukaryotic systems, it may be necessary to include other non-coding sequences or regulatory elements such as intervening sequences and poly-adenylation signals. Those skilled in the art will recognize and understand how to make fusion genes containing elements important to regulatory control of transcription and translation.

The fused genes encoding the binding agent and catalytic moiety can be ligated into a vector suitable for expression in either prokaryotic cells, eukaryotic cells, or both. Expression vehicles for production of the biocatalyst of this invention include plasmids or other vectors. For instance, suitable vectors for the fusion gene include plasmids of the types: pBR322, pEMBL plasmids, pEX plasmids, pBTac plasmids and pUC plasmids for expression in prokaryotic cells, such as *E. coli*.

A number of vectors exist for the expression of recombinant proteins in yeast. For instance, YEP24, YIP5 and YRP 17 are cloning and expression vehicles useful in the introduction of genetic constructs into *S. cerevisiae*. These vectors can replicate in *E. coli* due the presence of the pBR322 ori, and in *S. cerevisiae* due to the replication determinant of the yeast 2 micron plasmid. In addition, drug resistance markers such as ampicilin can be used.

The preferred mammalian expression vectors contain both prokaryotic sequences to facilitate the propagation of the vector in bacteria, and one or more eukaryotic transcription units that are expressed in eukaryotic cells. The pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. These vectors are modified with sequences from bacterial plasmids such as pBR322 to facilitate replication and drug resistance selection in both prokaryotic and eukaryotic cells. Alternatively, derivatives of viruses such the bovine papillomavirus (BPV-1), Epstein-Barr virus (pHEBo and p205) can be used for transient expression of proteins in eukaryotic cells. For other suitable expression systems for both prokaryotic and eukaryotic, see *Molecular Cloning*, 2nd Ed., ed. by Sambrook, Fritsch and Maniatis (Cold Spring Harbor Laboratory Press:1989) incorporated by reference herein.

In preferred embodiments, the expression vectors are chosen to include at least one selectable marker for each cell line in which the vector is to be replicated or expressed. For instance, the vectors can be derived with sequences conferring resistance to ampicillin, chloramphenicol or kanomycin to facilitate amplification in *E. coli*. For selection in mammalian cells, such markers as the mammalian expressible *E. coli* ecogpt gene—which codes for a xanthine-guanine phosphoribosyl transferase (XGPRT) and allows selection of transfected HPRT$^-$ mammalian cells with mycophenolic acid- can be utilized.

In the instance that the fusion protein is a hybrid molecule containing polypeptide sequences from a heavy or light chain from an antibody, fused to the polypeptide sequence of the catalytic moiety, it may be desirable to co-transfect and co-express the gene for the other chain of the antibody in the same cell. For example, if the fusion protein were a gamma heavy chain/trypsin hybrid, co-expression with the appropriate kappa or lambda light chain would facilitate the assembly of the antibody in vivo from the two exogenous transfected genes (see for example Rice et al. (1982) PNAS 79:7862; Oi et al. (1983) PNAS 80:825; and Morrison (1985) Science 229:1202, incorporated by reference herein).

It may necessary in some instances to introduce an unstructured polypeptide linker region between the catalytic moiety and binding agent fragments of the fusion protein. This linker can facilitate enhanced flexibility of the fusion protein allowing the catalytic moiety to freely interact with a surface component, reduce steric hindrance between the two fragments, as well as allow appropriate folding of each fragment to occur. The linker can be of natural origin, such as a sequence determined to exist in random coil between two domains of a protein. Alternatively, the linker can be of synthetic origin. For instance, the sequence $(Gly_4Ser)_3$ can be used as a synthetic unstructured linker. Linkers of this type are described in Huston et al. (1988) PNAS 85:4879; and U.S. Pat. No. 5,091,513, both incorporated by reference herein. Naturally occurring unstructured linkers of human origin are preferred as they reduce the risk of immunogenicity.

III. Methods of Testing Biocatalysts

Upon making the biocatalysts of the present invention, it will be desirable to test their efficacy. In addition to assaying the ability to block pathogenesis, it is desirable to compare the effect of the biocatalyst with a comparable concentration of the catalytic moiety alone.

Assays that are useful in scoring the efficiency and potency of the biocatalyst include both in vitro and in vivo assays. For example, in instances where the targeted surface component can be purified, the biocatalyst can be assessed by assays which measure binding to its cognate receptors where appropriate, or assays which monitor cleavage of the surface component, such as by SDS-PAGE.

The ability to inhibit pathogenesis in cell cultures can also be scored. For virus and other obligate intracellular parasites, uptake by host cells can be monitored. Survival of extracellular parasites can also be monitored in cell-free media.

Where appropriate, animal model systems can be used to assay in vivo effectiveness of the biocatalyst in preventing pathogenesis. For instance, mice or rats can be infected with a sample of pathogen that has been treated with the biocatalyst, with the catalytic moiety alone, or is untreated, and the pathologic manifestations of the pathogen can be assessed.

IV. Biocatalysts Directed Against HIV

One application of the biocatalyst of this invention is in the treatment of HIV. The pathogen-targeted biocatalyst is designed to specifically bind a surface component of the HIV virus, thus selectively delivering the enzymatic agent to a viral particle or infected cell expressing HIV coat proteins. For instance, a binding agent directed to the glycoproteins gp120, gp4l or uncleaved gp160 can be effective at targeting the catalytic moiety. The catalytic degradation of the structure of at least one of the HIV coat proteins can disrupt virion/host-cell and virally-infected-cell/host-cell interactions.

As detailed earlier, the CD4/gp120 interaction has been implicated in the mechanism of infectivity of the HIV virus. For the synthesis of a biocatalyst directed to the gp120 protein, a number of binding agents are useful. For instance, antibodies or binding fragments thereof which specifically recognize an epitope on gp120, or alternatively, a soluble fraction of the CD4 receptor capable of interacting with the CD4 binding site of gp120, are both useful binding agents for directing a catalytic activity to an important binding determinant of the HIV virus. One embodiment of a biocatalyst directed to the abrogation of HIV-1 pathogenicity involves the directed cleavage of the V3 loop. For instance, a suitable protease such as thrombin or trypsin is chemically coupled to a soluble fragment of CD4 in a manner yielding an enzymatically active molecule. A soluble CD4 fragment comprising the two most N-terminal domains E1 and E2 (also commonly referred to as V1 and V2) of CD4 is commercially available (American Biotechnologies, Inc. Catalog No. 013101). Alternatively, the most N-terminal domain, E1 (V1), can be cloned and expressed (see for example Poulin et al. (1991) *J Virol* 65:4893; and Chao et al. (1989) *J Biol Chem* 264:5812, incorporated by reference herein). Chemical linkage of the protease to the purified soluble CD4 (hereinafter "sCD4") protein can be accomplished using the cross-linking agents as described above.

Alternatively, instead of a chemical cross-linking agent, the HIV-1 biocatalyst can be constructed as a fusion protein. The extracellular fragment of CD4 exists as essentially 4 domains, with the two most N-terminal domains being implicated in the binding of gp120 (Arthos et al. (1989) *Cell*

57:469; and Ashkenazi et al. (1990) *PNAS* 87:7150). In fact, substantial gp120 binding is accomplished by the fragment comprising the first 100 amino residues of the N-terminus (the E1 domain). Between the E1 and E2 domain exists a short polypeptide sequence, approximately 10 residues long, which is believed to exist essentially as a random coil (Wang et al. (1990) *Nature* 348:411). By ligating the gene coding for the protease or a catalytically active fragment thereof to the 3' end of the gene coding for the first 111 amino acid residues of CD4 (see Chao et al. (1989) *J BiolChem* 264:5812) a non-structured polypeptide linker is incorporated. Appropriate expression vectors and host cells will be apparent to those skilled in the art.

For both chemical and genetic fusion of the protease and sCD4 fragment, those skilled in the art will recognize the need to control the attachment site and the level of flexibility at the coupling site. Steric hindrance can affect the catalytic activity of the enzyme as well as the association constant for binding of the CD4 fragment. In choosing the cross-linking agents, the length of the linker bridge and the attachment sites to the protein molecules is of importance. For the construction of fusion proteins, the effect of heterogenous sequences on the folding of both the enzyme and the CD4 fragments should be considered.

Other binding agents useful in the directed degradation of the V3 loop include antibodies directed against the CD4 binding site of gp120 (see for example Tilley et al. (1991) *Res Virol* 142:247; Ohno et al. (1991) *PNAS* 88:10726; and Javaherian et al. (1990) *Science* 250:1590, incorporated by reference herein). These antibodies can be chimeric antibodies, or binding fragments as described above. Appropriate linkers will be apparent.

A number of techniques have been developed that allow for screening the effectiveness of the biocatalyst constructs in vitro. Examples of binding assays include: i). ELISA-type assays in which CD4 binding to immobilized gp120 is scored after treatment with either free enzyme or the biocatalyst construct. The immobilized gp120 is incubated with either the enzyme or the biocatalyst construct. The enzyme or biocatalyst is then washed away, and the level of CD4 binding is measured either directly by using labeled sCD4 (such as FITC-labeled CD4 available from American Biotechnologies Inc. Catalog No 013003) or indirectly as in a sandwich-type assay using sCD4 followed by a labeled anti-CD4 antibody. ii). Competition binding assays in which the binding of labeled-gp120 to sCD4 is scored against the binding of gp120 treated with either free enzyme of the biocatalyst construct.

In addition, in vitro biological assays can be used to measure the ability of the biocatalyst to disrupt HIV infectivity. For instance, viral neutralization assays can be carried out in which cell cultures are incubated with viral stocks which have been treated with the biocatalyst. The infectivity of biocatalyst-treated virus, untreated virus, and virus treated with free enzyme can be assessed by means such as reverse transcriptase assays (Ohno et al. (1991) *PNAS* 88:10726).

Syncytium assays can also be used to assess the ability of the biocatalyst to inactivate CD4 binding of gp120 relative to the free enzyme. Briefly, cells chronically infected with HIV-1 are incubated with dilutions of the biocatalyst. Cells susceptible to syncytia, such as C8166 cells are then added and incubated with the infected cells. Syncytium greater than three lymphocyte cell diameters score as positives, and the number of syncytium compared to that obtained with untreated infected cells or free-enzyme treated infected cells (Richman et al. (1990) AIDS Research and Reference Reagent Program, Courier No 90-01, pages 6–9, incorporated by reference herein).

Most conventional approaches in designing HIV therapies directed to disrupting the gp120/CD4 interaction have involved masking molecules such as sCD4. One advantage of the present invention in targeting the degradation of the envelope protein gp120 with the selective delivery of a catalytic moiety comes from the fact that normal function of the T cells in the immune system would not be affected. In the case of sCD4 therapy, the presence of large amounts of soluble CD4 or derivatives, due to the stoichiometric dependency of this therapy, could compete with the endogenous CD4 of the T cells and therefor adversely affect the performance of the cells in immune response. Indeed, for reasoned described above, the use of any masking molecules meant to bind determinants recognized by CD4 will encounter this problem. The approach of the present invention is more desirable in that the concentration of binding molecules can be considerably smaller due to the catalytic nature of action of the biocatalyst.

The biocatalyst of the present invention can be delivered along with a pharmaceutically acceptable carrier. Appropriate pharmaceutical carriers will be apparent to those skilled in the art. The dosage concentration of the biocatalyst is determined such that pathogenecity is abrogated. Factors involved in determining a dosage regimen for the administration of the biocatalyst include the minimum effective concentration as well as the clearance of the biocatalyst from circulation. These factors can be determined by the skilled artisan without undue experimentation.

EXAMPLE 1

A CD4 gene encoding an amino-terminal fragment of CD4 was constructed as follows. The oligonucleotides designated below as CD4-01 through CD4-16 were synthesized by standard nucleic acid synthesis techniques.

CD4-01 (SEQ ID No. 11) AATTCATGAAGAAAGTAG-TACTTGGCAAGAAA

CD4-02 (SEQ ID No. 12) GGCGATACAGTGGAGCT-CACGTGCACAGCTAGCCAGAAGAAGAGCATT

CD4-03 (SEQ ID No. 13) CAATTCCACTGGAA-GAACTCCAACCAGATTAAGATCCTTGGTAACCAA

CD4-04 (SEQ ID No. 14) GGTAGCTTCTTAAC-TAAGGGCCCATCCAAGCTTAACGATCGCGCTGAC

CD4-05 (SEQ ID No. 15) TCTCGTCGTAGCCTTTGG-GACCAAGGTAACTTTCCAACTGATCATCAAG

CD4-06 (SEQ ID No. 16) AATCTTAAGATCGAA-GACTCTGATACGTATATCTGTGAAGTAGAGGAT

CD4-07 (SEQ ID No. 17) CAGAAAGAGGAAGT-TCAACTGCTAGTATTCGGCCTGACTGCCAACAGT

CD4-08 (SEQ ID No. 18) GACACCCATCTGCTG-CAGGGCTAATAG

CD4-09 (SEQ ID No. 19) GATCCTATTAGCCCTGCAG

CD4-10 (SEQ ID No. 20) CAGATGGGTGTCACTGTTG-GCAGTCAGGCCGAATACTAGCAGTTGAAC

CD4-11 (SEQ ID No. 21) TTCCTCTTTCTGATCCTC-TACTTCACAGATATACGTATCAGAGTCTTC

CD4-12 (SEQ ID No. 22) GATCTTAAGATTCTTGAT-GATCAGTGGAAAGTTACCTTGGTCCCAAAG

CD4-13 (SEQ ID No. 23) GCTACGACGAGAGT-CAGCGCGATCGTTAAGCTTGGATGGGCCCTTAGT

CD4-14 (SEQ ID No. 24) TAAGAAGCTACCTTGGTTAC-CAAGGATCTTAATCTGGTTGGAGTTCTT

CD4-15 (SEQ ID No. 25) CCAGTGGAATTGAATGCTCT-TCTTCTGGCTAGCTGTGCACGTGAGCTC

CD4-16 (SEQ ID No. 26) CACTGTATCGCCTTTCTTGC-CAAGTACTACTTTCTTCATG 300 pmoles each of oligonucleotides CD4-1 through CD4-16 were mixed with ONE-PHORALL buffer (Pharmacia, Piscataway, N.J.), 1 mM ATP (final Concentration) and 10 units of T4 Polynucleotide kinase (Pharmacia, Catalog No. 27-0736-01) in a reaction volume of 30 μL. The reaction mixture was incubated for 1 hour at 37° C.

After phosphorylation of the oligonucleotides, the reaction tube was placed into a boiling water bath, the heater turned off, and the water bath allowed to cool to room temperature in order to facilitate annealing of complementary sequences within the olignucleotide mixture. After annealing, ligation buffer (BRL, Gaithersburg, Md.) and I Unit T4 DNA ligase (BRL Catalog No. 52245B) was added to the tube and the tube held at room temperature for 4 hours. After ligation, 3 uL aliquots were removed and analyzed on a 1% agarose gel to verify assembly. The sequence of the final assembly is shown in FIG. 1 (SEQ ID No. 1).

The ligation mixture was cleaned once with phenolchloroform and once with chloroform, and the DNA was precipitated with 2 volumes EtOH. The pellet was resuspended in water and the CD4-DNA, as well as lug of pBluescript 11 KS (Stratagene, N.J.) were digested with EcoRI and BamHI. After completion of the digest, the DNA was separated on an agarose gel, the bands cut out and purified with GENECLEAN. Equimolar concentrations of CD4 construct and vector (100 ng total) were ligated at 17° C for 16 hours. The ligated mix was then diluted 5x with water and 2 uL of this mix were used to transform 50 uL of competent JM109 cells.

EXAMPLE 2

The protein A "Z" domain/enterokinase cleavage recognition (EKCR) sequence/CD4 fusion gene was constructed as follows:

The double stranded oligonucleotide (SEQ ID No. 2)

5'- AATTCCGACGACGATGACAAATC -3'

3'- GGCTGCTGCTACTGTTTAGGTAC -5' was digested with NcoI, and ligated to the BspHI site at the 5' end of the CD4 construct shown in FIG. 1.

The resulting EKCR/CD4 fusion gene was than ligated into the EcoRI and SalI sites of pEZZ-18 (Pharmacia Catalog No. 27-4810-01) using the EcoRI and PstI overhangs created by treating the CD4 fusion gene with the corresponding restriction endonucleases. The pEZZ-1 8 vector contains the protein A signal sequence and two synthetic "Z" domains which are based on the "B" IgG binding domain of protein A. This construct allows "ZZ" fusion proteins to be secreted from *E. coli* and to have increased solubility in aqueous environments. Thus, the resulting fusion gene encodes a ZZ/EKCR/CD4 fusion protein. The protein A sequences can be removed from CD4 by treatment of the resulting fusion protein with enterokinase. See Su et al. (1992) *Biotechniques* 13:756; and Forsberg et al. (1992) *J Protein Chem* 11:201, incorporated by reference herein.

EXAMPLE 3

A gene fragment encoding the catalytic domain of human tissue-Plasminogen Activator (tPA) was isolated by PCR amplification of a discrete portion of a human tPA cDNA clone. See *Molecular Cloning: A Laboratory Manual* 2d Ed., ed. by Sambrook, Fritsch and Maniatis (CSH Press: 1989), chapter 5, 6, and 14, incorporated by reference herin. Using the 5'-amplimer (SEQ ID No. 3) and 3'-amplimer (SEQ ID No. 4) shown in FIG. 2, the catalytic domain fragment of tPA was amplified from the plasmid ptPA-trp12 (ATCC No. 40404). See Pennica et al. (1983) *Nature* 301:214, incorporated by reference herein. The final amplification product contained the nucleotide sequence of Ser262 through Pro527. In addition, by design of the above amplimers, the 5' end of the amplification product included a HindIII and an NsiI restriction endonuclease site, as well as the CD4 carboxy terminal sequence downstream of the PstI site in the CD4 construct of FIG. I (SEQ ID No. 1). The 3' end of the amplification product, directly downstream of the stop codon for the tPA domain, contained an XhoI and a BamHI restriction endonuclease cleavage site.

Figure 3:
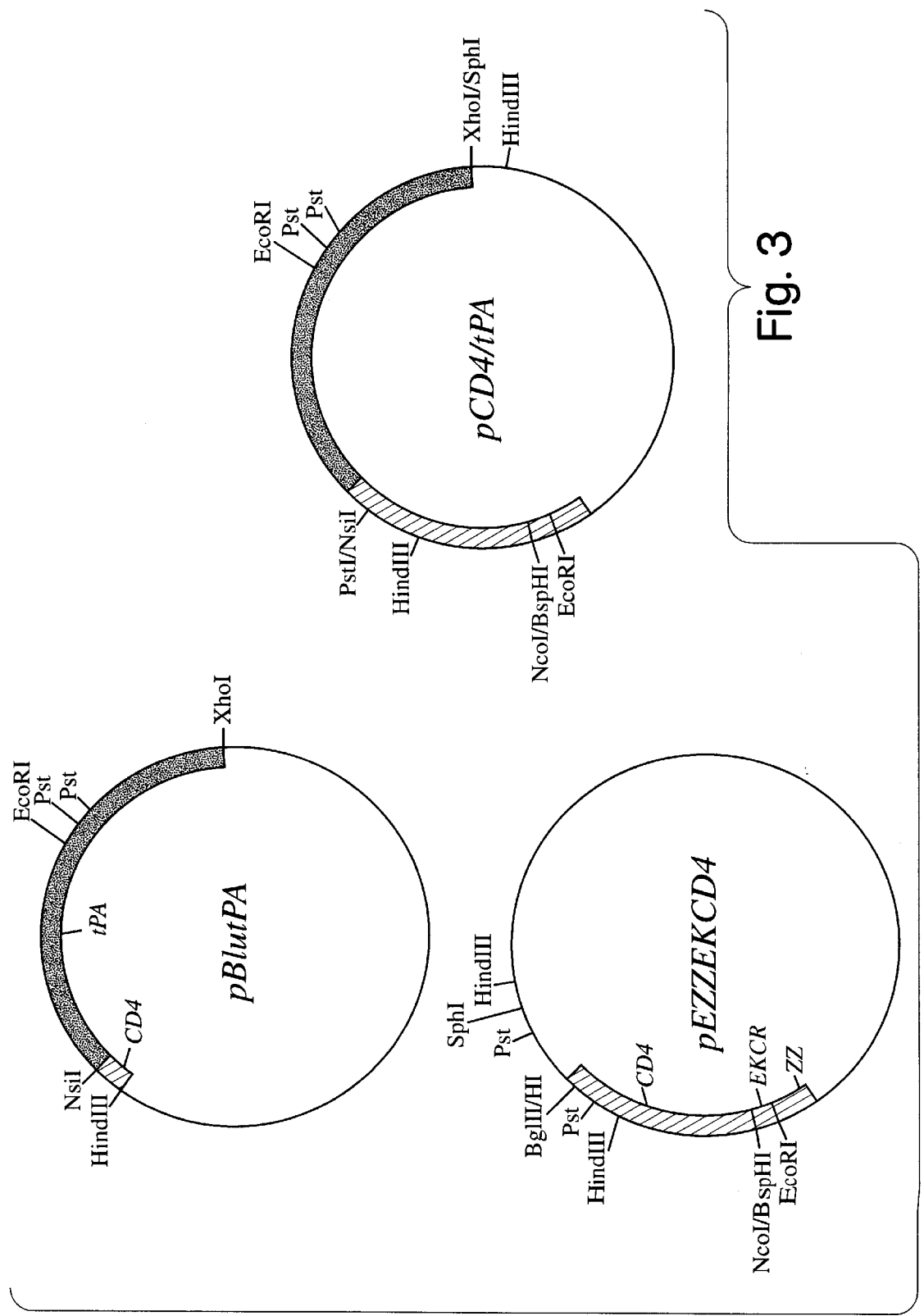
FIG. 3 shows various plasmids used to create a CD4/tPA fusion protein.

This amplified catalytic domain fragment was ligated into pBluescript II KS via its 5' HindIII and 3' XhoI sites to create the replicable vector pBlutPA. (see FIG. 3)

EXAMPLE 4

To create the CD4/tPA fusion gene, the tPA gene fragment was excised from pBlutPA. The vector was first cut with XhoI and treated with Klenow to create a blunt end. Subsequently, the linearized vector was cut with NsiI leaving a 5' "sticky end". The products were run out on an agarose gel and the NsiI/XhoI tPA fragment isolated.

Next, the pEZZEK/CD4 vector was digested with SphI then treated with T4 Polymerase to create blunt ends at the SphI cleavage site. The linearized vector was then cut with PstI, which cleaved at the PstI site indicated at the 3' end of the CD4 construct of FIG. 1, and the remaining plasmid isolated.

The NsiI/Xhol tPA fragment was then ligated into the PstI/SphI treated pEZZEKCD4 plasmid to create the new vector pCD4/tPA.

The vector pCD4/tPA (FIG. 3) codes for a fusion protein having an overall fusion assembly including from amino terminus to carboxy terminus, the protein A secretory and "Z" domains, an enterokinase cleavage recognition sequence, a CD4 domain, and the catalytic domain of tPA. The nucleic acid sequence (SEQ ID No. 5), and corresponding amino acid sequence (SEQ ID No. 6), for the CD4/tPA portion of the fusion gene is shown in FIGS. 4A and 4B.

Purified PCD4/tPA plasmid was used to transform competent XL 1-Blue cells (Stratagene Catalog No. 200268). The transformed cells were cultured, and the CD4/tPA fusion protein isolated from the cell supernatant using an IgG Sepharose 6FF column. The "ZZ" domain is bound tightly by IgG Sepharose 6FF (Pharmacia Catalog No. 17-0909-01), thus allowing one-step purification of expressed proteins, see Lowenadler et al. (1987) *Gene* 58:87, incorporated by reference herein. The purified fusion protein was assayed and shown to have crude proteolytic activity by its ability to digest casein in agar diffusion plates (Bio-Rad Catalog No. 500-0011).

EXAMPLE 5

In a manner similar to that used in the construction of the CD4/tPA fusion protein, a CD4/thrombin fusion protein can be generated. Beginning with a human liver CDNA library (Stratagene Catalog No. 937200), a catalytic fragment of thrombin can be obtained by PCR amplification using the 5' (SEQ ID No. 7) and 3' (SEQ ID No. 8) amplimers shown in FIG. 5. The PCR product includes Ile321 through Glu579 of thrombin (see Friezner et al. (1983) *Biochemistry* 22:2087, incorporated by reference herein) as well as an NsiI endonuclease site and the carboxy-terminus of CD4 at its 5' end and an XhoI endonuclease site at its 3' end due to their presence in the PCR amplimers. As described above, the thrombin gene fragment can be ligated into pEZZEK/CD4 to yield a CD4/thromnbin fusion gene. The sequence of the CD4/thrombin portion of the fusion gene and the corresponding amino acid sequence is given in FIGS. 6A and 6B (SEQ ID Nos. 9 and 10).

EXAMPLE 6

Urokinase (UK) type plasminogen activator is a highly restricted serine protease whose principal substrate is plasminogen. The cleavage site or enzyme binding site for UK consists of a loop on plasminogen with the following sequence: CPGR-VVGGC in which cleavage occurs between arginine$^{560}$ and Valine$^{561}$. This plasminogen cleavage site loop is highly homologous to a conserved region of the $V_3$ loop.

The effect of urokinase on the infectivity of HIV was tested. Briefly, the standard MT-2-cytotoxicity assay was used to determine HIV infectivity of MT-2 cells. Two methods of exposure of UK, virus and cells were employed:

Method 1: HIV-1 virus (1:2 dilution) was incubated with MT-2 cells (2×10$^5$/ml) in the presence of a range of concentrations (0–8 μM) of high molecular weight (HMW) UK or other test enzymes for 5 days. The cells and virus were centrifuged and washed daily and fresh media with enzyme was added. At the end of 5 days, the surviving cells were measured by MTT.

Method 2: HIV-1 virus was incubated with or without HMW-UK or other test enzymes for 15–60 minutes and then incubated with MT-2 cells (2×10$^5$/ml) for 5 days. No additional enzymes were added during the virus-cell incubation. Surviving cells were again measured by MTT.

The percent inhibition of infectivity by the enzyme was calculated from the control value determined from virus plus MT-2 cells alone. All experiments were done in triplicate.

Figure 7:
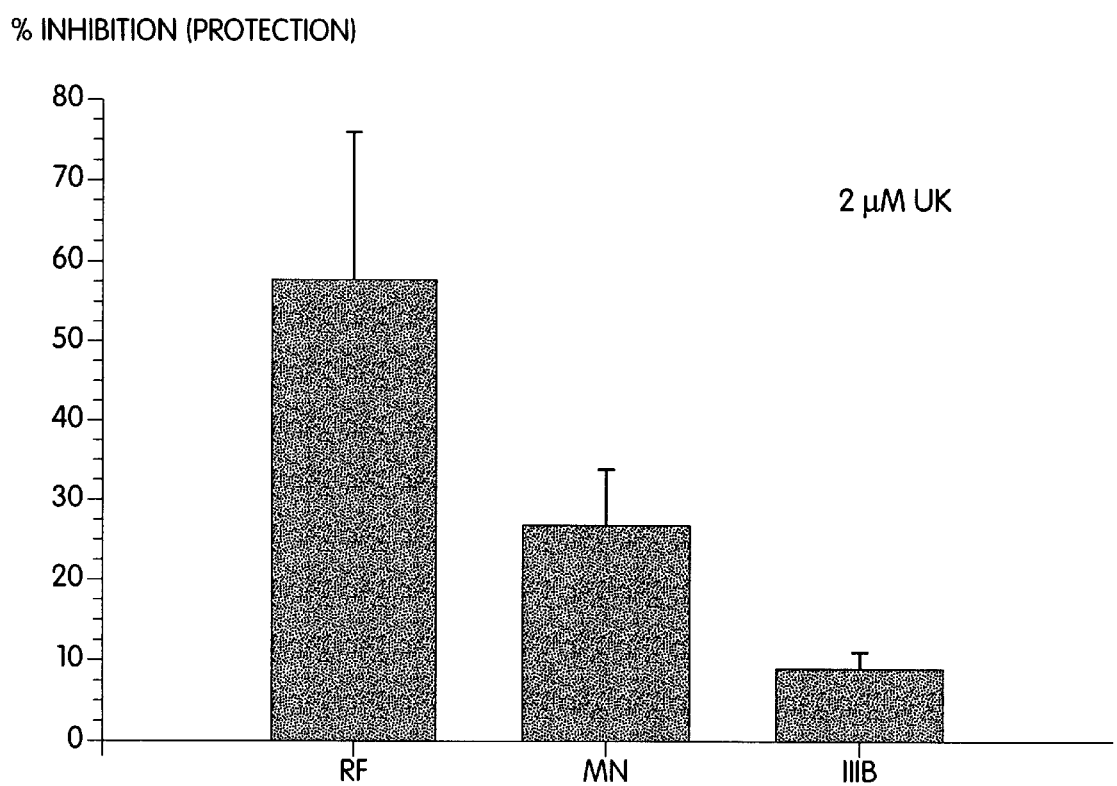
FIG. 7 illustrates strain specificity of inhibition by arokinase (UK) (mean and 2 SD). Three strains (RF, MN, and IIIB) of HIV-1 virus ($2.7 \times 10^{11}$ virus/ml) were incubated with MT-2 t cells ($2 \times 10^5$/ml) in the absence or presence of UK (2 $\mu$M) for 5 days. The cells and virus were centrifuged and washed daily and fresh media with UK was added. At the end of 5 days, the surviving cells were measured with 3-[4,5-Dimethylthiazol-2-Y1]-2,5-diphenyltetrazolium bromide; thiazolyl blue (MTT). The percent inhibition of infectivity by the UK was calculated from the control value in the absence of UK. All experiments were done in triplicate at least twice.

As shown in FIG. 7, inhibition by 2 μM UK was viral strain specific with the RF strain being the most sensitive to the inhibitory effect of UK. The RF strain is also the one most closely homologous to plasminogen.

Figure 8:
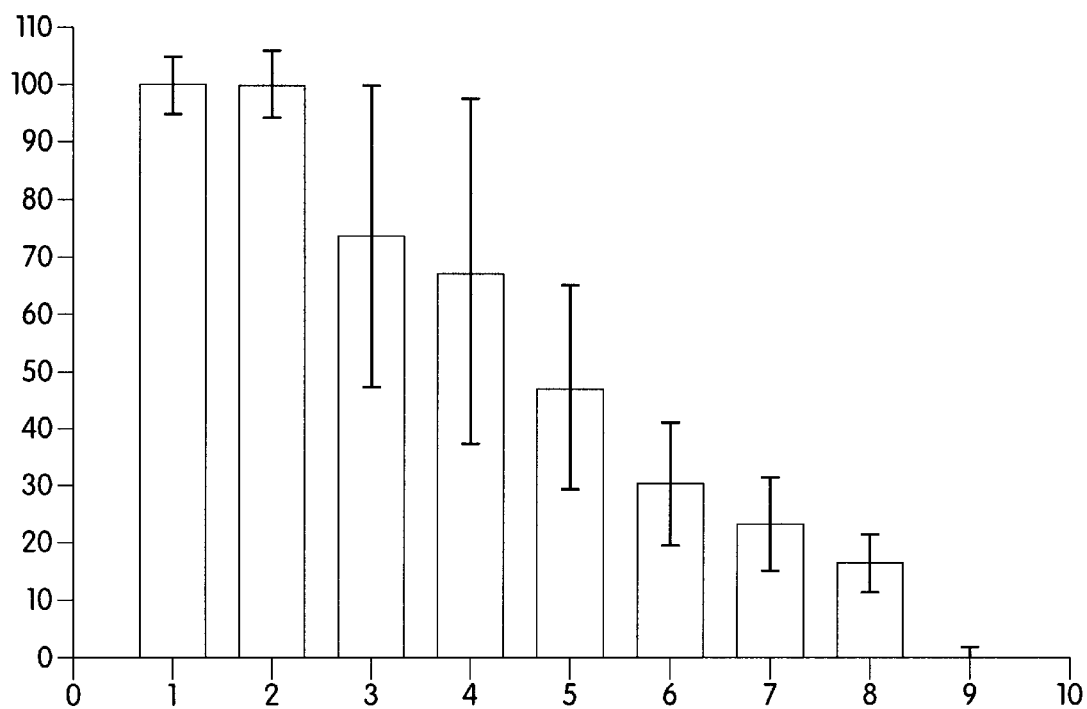
FIGS. 8 and 9 show the concentration-dependence and time-dependence of inhibition by UK.
Figure 9:
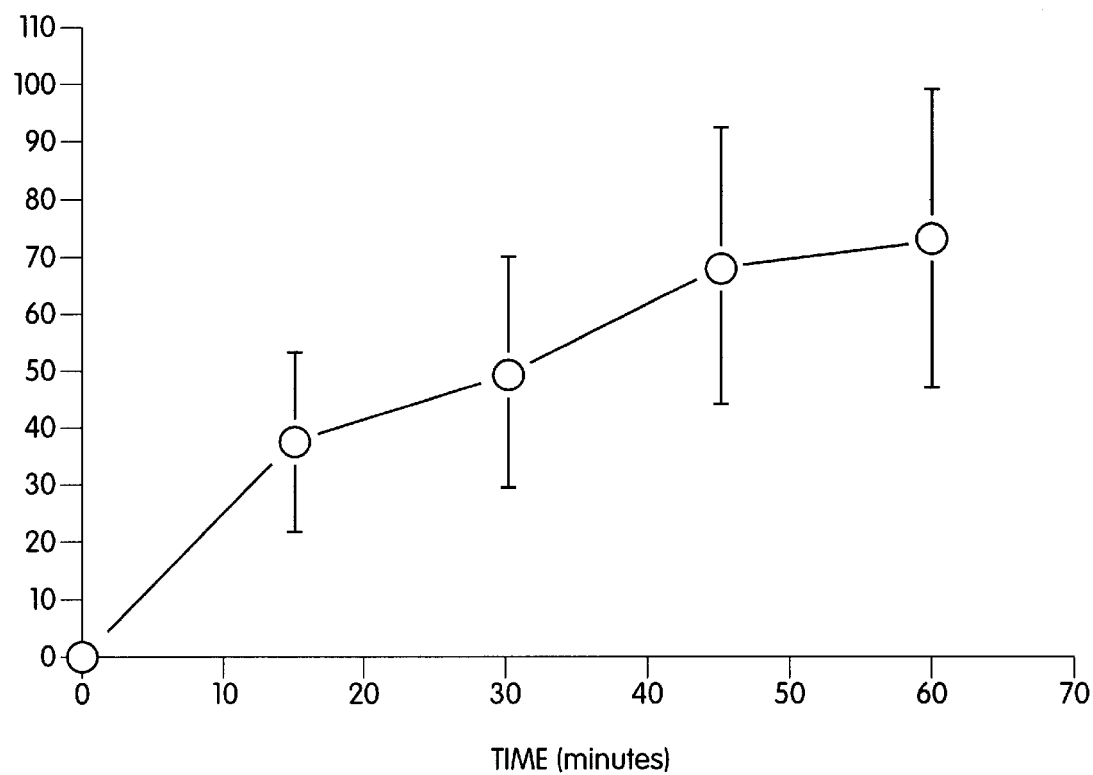

The inhibitory effect of UK on RF strain cell infectivity (using Method 2) was dose dependent ranging from ~100% at 4–8 μM UK to ~18% at 0.02 μM UK (FIG. 8). The UK effect was also found to be time-dependent, reaching a plateau in about 45–60 minutes as shown in FIG. 9 in which 2 μM UK was incubated with virus (RF strain) for 15–60 minutes prior to the incubation of virus with MT-2 cells.

Figure 10:
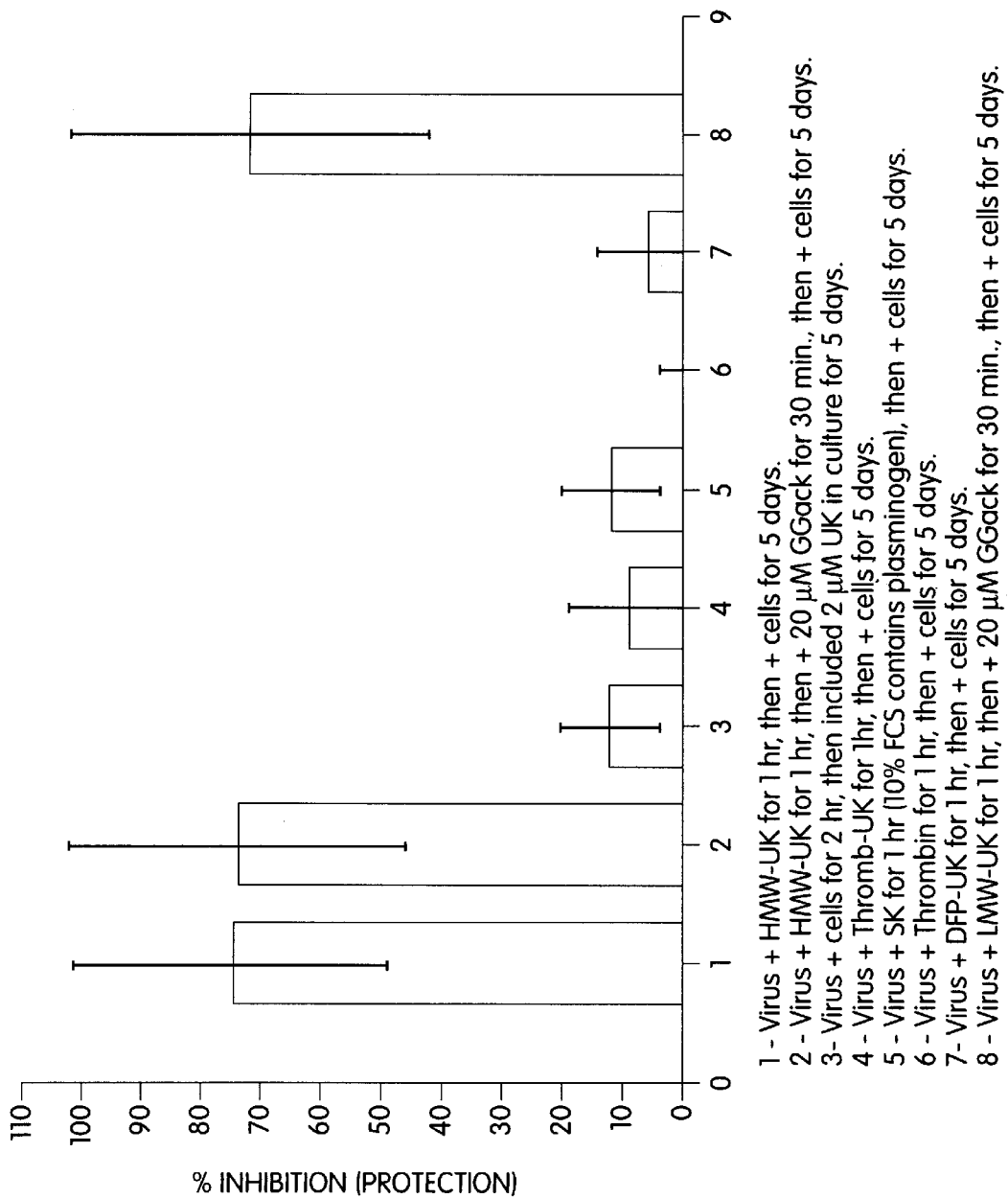
FIG. 10 shows the inhibitory effects of UK and other proteases on infectivity of HIV-1RF. $2.7 \times 10^{10}$ virus/ml) was incubated with 2 $\mu$M enzyme+/−inhibitors and then incubated with MT-2 cells for 5 days as described in FIGS. 8 and 9 above.

The experiments illustrated in FIG. 10 indicate that the UK (HMW-UK or LMW-UK) effect is specific, catalytic, and on the HIV-1 itself (independent of the virus-cell interaction). That is, other serine proteases like thrombin or streptokinase (SK:plasminogen activator complex) had little or no effect, at least on this strain of HIV. Inactivation of UK by diisopropylflurophosphate (DFP) nullified the effect of UK (column 7) as did the use of thrombin-cleaved pro-urokinase (thromb-UK), a catalytically inactive form of UK, shown in column 4. When the UK was inhibited by the addition of a specific inhibitor (GGack) one hour after exposure to the virus (column 2), full inhibition was retained indicating that viral inactivation had occurred within the first hour, before the addition of GGack. This conclusion is supported by the observation that when cells were exposed to virus prior to introduction of the UK (column 3), essentially no inhibition of infectivity took place.

Virus titration studies using H9 cells and the p24 antigen assay were also performed. Those studies were done since it was determined that the H9 cells, in contrast to the MT-2 cells, have a high affinity (0.25 nM) receptor for HMW-UK (probably representing the well established u-PA cell receptor). A similar u-PA receptor was also demonstrated on the virus itself by studies with radiolabeled pro-UK or HMW-UK.

Figure 11:
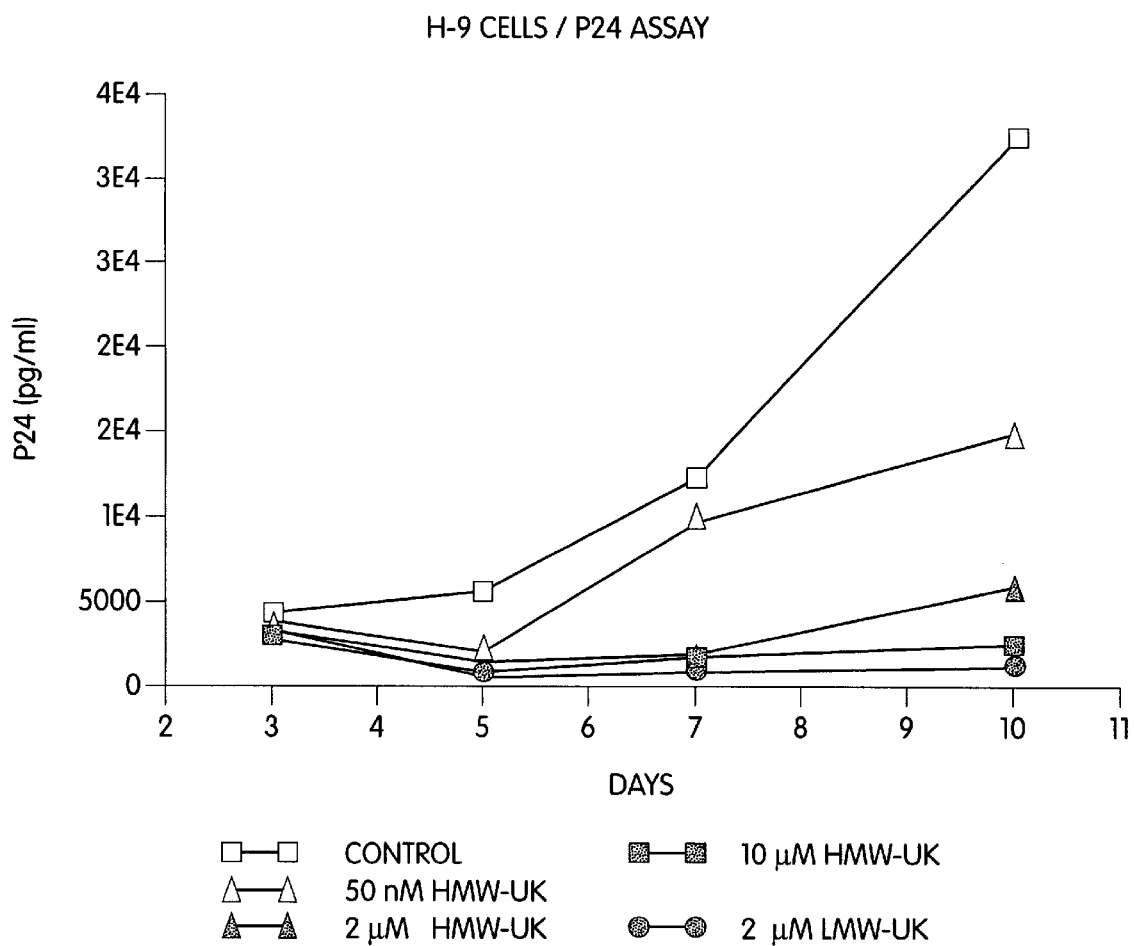
FIG. 11 shows the effect of UK and LMW-UK on the reproduction of HIV-1RF in H-9 cells. $2 \times 10^{5/ml}$ H-9 cells were incubated with HIV-1RF ($2.7 \times 10^{10}$ virus/ml)+/−UK or LMW-UK for 4 hours. Cells were then washed and resuspended in 1 ml growth media containing the same concentrations of enzymes, and incubated at 37° C. Cells were split at days 3 and 7 and adjusted to $2 \times 10^5$/ml in media+/− enzymes. The supernatants were harvested at days 3, 5, 7, and 10, and p24 antigen measured (DuPont-NEN). ■ control; ◇ UK (50 nM); ▽ UK (2 μM)+DFP-UK (20 μM); ◆ UK (2 μM); □ UK (10 μM); ● LMW-UK (2 μM).

As shown in FIG. 11, a dose dependent suppression or viral reproductivity was found with HMW-UK. However, the most effective suppression occurred with LMW-UK. In the presence of 2 μM LMW-UK, the p24 antigen level was only 4% that present in the control. In the presence of 2 μM HMW-UK, the p24 level was 18% that of the control. Since LMW-UK does not bind to the u-PA cell receptor, these findings indicate that the cell receptor for UK does not promote the inhibitory effect of UK on HIV infectivity of H-9 cells.

These result demonstrate that enzymatic cleavage of the crown of the $V_3$ loop of gp120, by UK or its derivatives inhibits HIV-1 cell infectivity. This cleavage can be accomplished by UK. However, the efficiency of this reaction for UK is dependent on the next residue and is most efficient for HIV-1 strains in which the adjacent residue is Valine. However, modification of the active site of UK to make the enzyme less restricted can be used to solve the problem of dealing with the great majority of HIV-1 strains which have Alanine at position 323. Modification of the active site of UK will also make it a far less efficient plasminogen activator, which is desirable to avoid the side effects associated with non-specific plasminogen activation.

The Equivalents

Those skilled in the art will recognize, or be able to ascertain using no more than routine experimentation, numerous equivalents to the specific procedures described herein. Such equivalents are considered to be within the scope of this invention and are covered by the following claims.

What is claimed is:

1. A virus-targeted biocatalyst for disrupting, interactions between the surface components of a virus and a host cell by degrading a surface component of the virus, comprising a binding agent specific for a surface component of the virus and an enzyme, or a catalytically- active fragment thereof, which degrades a surface component sufficiently to abrogate viral pathogenicity, wherein the biocatalyst is not consumed after degradation of the surface component.

2. A virus-targeted biocatalyst of claim 1, wherein the binding agent is an antibody, or a binding fragment thereof, specific for the surface component of the virus.

3. A virus-targeted biocatalyst of claim 2, wherein the antibody or binding fragment thereof, is selected from the group consisting of:
    a) an individual chain antibody of heavy chain origin;
    b) an individual chain antibody of light chain origin;
    c) a variable region or portion thereof from an L chain ($V_L$) or an H chain ($V_H$);
    c) an Fab, Fv, sFv or $F(ab)_2$ fragment; and
    d) an HL monovalent fragment.

4. A virus-targeted biocatalyst of claim 1, wherein the binding agent is a receptor, or binding domain thereof, for the surface component of the virus.

5. A virus-targeted biocatalyst of claim 1, wherein the binding agent is selected from the group consisting of polycationic molecules, polyanionic molecules and hydrophobic molecules.

6. A virus-targeted biocatalyst of claim 1, wherein the binding agent is a polyanionic molecule selected from the group consisting of polynucleotides, polysaccharides and polyanionic peptides.

7. A virus-targeted biocatalyst of claim 1, wherein the virus is HIV.

8. A virus-targeted biocatalyst of claim 7, wherein the binding agent is an antibody, or fragment thereof, which is specific for gp120.

9. A virus-targeted biocatalyst of claim 7, wherein the binding agent is CD4, or a gp120 binding domain thereof.

10. A virus-targeted biocatalyst of claim 9, wherein the gp120 binding domain of CD4 is selected from the group consisting of the E1 through E2 domain of CD4 and the E1 domain of CD4.

11. A virus-targeted biocatalyst of claim 1, wherein the enzyme, or a catalytically-active fragment thereof, is chosen from the group consisting of proteases, lipases and glycosidases.

12. A virus-targeted biocatalyst of claim 1, wherein the virus-targeted biocatalyst is a fusion protein.

13. A virus-targeted biocatalyst of claim 1, wherein the binding agent and the enzyme, or a catalytically-active fragment thereof, are covalently joined by a chemical cross-linking agent.

14. A biocatalyst targeted to HIV for disrupting interactions between the surface components of HIV and a host cell by degrading a surface component of HIV, comprising a binding agent specific for gp120 coupled to a protease, or a catalytically-active fragment thereof, which degrades gp120 sufficiently to abrogate HIV pathogenicity, wherein the biocatalyst is not consumed after degradation of gp120.

15. An HIV-1-targeted biocatalyst of claim 14, wherein the binding agent is an antibody, or a fragment thereof, specific for gp120.

16. An HIV-1-targeted biocatalyst of claim 14, wherein the binding agent is specific for the CD4 region of gp120.

17. An HIV-targeted biocatalyst of claim 14, wherein the binding agent is CD4, or a gp120 binding domain thereof.

18. An HIV-targeted biocatalyst of claim 17, wherein the gp120 binding domain of CD4 is selected from the group consisting of the E1 through E2 domain of CD4 and the E1 domain of CD4.

19. An HIV-targeted biocatalyst of claim 14, wherein the HIV-targeted biocatalyst is a fusion protein.

20. An HIV-1-targeted biocatalyst of claim 14, wherein the binding agent and the protease, or catalytic domain thereof, are covalently joined by a chemical cross-linking agent.

21. A virus-targeted biocatalyst for disrupting interactions between the surface components of a virus and a host cell by degrading a surface component of the virus, comprising a fusion protein comprising
    A. a binding agent which specifically binds a surface component of a viral pathogen,
    B. a catalytic moiety which degrades a component of the viral pathogen, and
    C. a linker sequence linking the binding agent and the catalytic moiety
wherein degradation of the component of the viral pathogen by the biocatalyst results in abrogation of viral pathogenicity, and wherein the biocatalyst is not consumed after degradation of the surface component.

22. A virus-targeted biocatalyst of claim 21, wherein the linker sequence is a synthetic unstructured peptide sequence.

23. A virus-targeted biocatalyst of claim 21, wherein:
    A. the virus is HIV,
    B. the binding agent is selected from the group consisting of (i) an antibody specific for gp120, (ii) an antibody fragment specific for gp120, and (iii) CD4, or a fragment of thereof which specifically binds gp120, and
    C. the catalytic moiety is selected from the group consisting of proteases, lipases, and glycosidases
wherein selective degradation of gp120 results in abrogation of HIV infectivity.

24. A virus-targeted biocatalyst of claim 23, wherein the fusion protein further comprises a linker sequence between the binding agent and the catalytic moiety.

25. A hybrid DNA encoding the virus-targeted biocatalyst of claim 21, comprising DNA encoding a binding agent which specifically binds a surface component of the virus and DNA encoding a catalytic moiety which degrades a component of the virus such that pathogenicity is abrogated.

26. A virus-targeted biocatalyst of claim 21, wherein the linker sequence is a naturally occuring unstructured peptide sequence.

27. A biocatalyst targeted to HIV for disrupting interactions between the surface components of HIV and a host cell by degrading a surface component of HIV, comprising a fusion protein including the amino acid sequence of FIGS. 4A and 4B (SEQ ID No. 6) or a functional portion thereof or a homolog having substantial sequence identity therewith, wherein the biocatalyst is not consumed after degradation of the surface components.

28. A biocatalyst targeted to HIV for disrupting interactions between the surface components of HIV and a host cell by degrading a surface component of HIV, comprising a fusion protein including the amino acid sequence of FIGS. 6A and 6B (SEQ ID No. 10) or a functional portion thereof or a homolog having substantial sequence identity therewith, wherein the biocatalyst is not consumed after degradation of the surface components.

* * * * *

SEQUENCE LISTING (1) GENERAL INFORMATION:

(iii) NUMBER OF SEQUENCES: 26

(2) INFORMATION FOR SEQ ID NO:1:

(i) SEQUENCE CHARACTERISTICS:
      (A) LENGTH: 351 base pairs
      (B) TYPE: nucleic acid
      (C) STRANDEDNESS: double
      (D) TOPOLOGY: linear (ii) MOLECULE TYPE: cDNA (xi) SEQUENCE DESCRIPTION: SEQ ID NO:1:

| | |
|---|---|
| AATTCATGAA GAAAGTAGTA CTTGGCAAGA AAGGCGATAC AGTGGAGCTC ACGTGCACAG | 60 |
| CTAGCCAGAA GAAGAGCATT CAATTCCACT GGAAGAACTC CAACCAGATT AAGATCCTTG | 120 |
| GTAACCAAGG TAGCTTCTTA ACTAAGGGCC CATCCAAGCT TAACGATCGC GCTGACTCTC | 180 |
| GTCGTAGCCT TTGGGACCAA GGTAACTTTC CACTGATCAT CAAGAATCTT AAGATCGAAG | 240 |
| ACTCTGATAC GTATATCTGT GAAGTAGAGG ATCAGAAAGA GGAAGTTCAA CTGCTAGTAT | 300 |
| TCGGCCTGAC TGCCAACAGT GACACCCATC TGCTGCAGGG CTAATAGGAT C | 351 |

(2) INFORMATION FOR SEQ ID NO:2:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: other nucleic acid (xi) SEQUENCE DESCRIPTION: SEQ ID NO:2:

| | |
|---|---|
| AATTCCGACG ACGATGACAA ATCCATG | 27 |

(2) INFORMATION FOR SEQ ID NO:3:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:3:

| | |
|---|---|
| GGAAGCTTAT GCATGGCCAG TCCCTGACAC TGTCCACCTG CGGCCTGAGA CAGTAC | 56 |

(2) INFORMATION FOR SEQ ID NO:4:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:4:

| | |
|---|---|
| CCGCGCTCGA GGGATCCCTA TCACGGTCGC ATGTTGTCAC G | 41 |

(2) INFORMATION FOR SEQ ID NO:5:

(i) SEQUENCE CHARACTERISTICS:
        (A) LENGTH: 1163 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 3..1151

(xi) SEQUENCE DESCRIPTION: SEQ ID NO:5:

| | |
|---|---|
| TC ATG AAG AAA GTA GTA CTT GGC AAG AAA GGC GAT ACA GTG GAG CTC | 47 |

|  |  |
|---|---|
| Met Lys Lys Val Val Leu Gly Lys Lys Gly Asp Thr Val Glu Leu<br>1              5                    10               15 |  |
| ACG TGC ACA GCT AGC CAG AAG AAG AGC ATT CAA TTC CAC TGG AAG AAC<br>Thr Cys Thr Ala Ser Gln Lys Lys Ser Ile Gln Phe His Trp Lys Asn<br>                    20                  25                   30 | 95 |
| TCC AAC CAG ATT AAG ATC CTT GGT AAC CAA GGT AGC TTC TTA ACT AAG<br>Ser Asn Gln Ile Lys Ile Leu Gly Asn Gln Gly Ser Phe Leu Thr Lys<br>                    35                  40                  45 | 143 |
| GGC CCA TCC AAG CTT AAC GAT CGC GCT GAC TCT CGT CGT AGC CTT TGG<br>Gly Pro Ser Lys Leu Asn Asp Arg Ala Asp Ser Arg Arg Ser Leu Trp<br>      50                  55                  60 | 191 |
| GAC CAA GGT AAC TTT CCA CTG ATC ATC AAG AAT CTT AAG ATC GAA GAC<br>Asp Gln Gly Asn Phe Pro Leu Ile Ile Lys Asn Leu Lys Ile Glu Asp<br>      65                  70                  75 | 239 |
| TCT GAT ACG TAT ATC TGT GAA GTA GAG GAT CAG AAA GAG GAA GTT CAA<br>Ser Asp Thr Tyr Ile Cys Glu Val Glu Asp Gln Lys Glu Glu Val Gln<br>80                    85                  90                  95 | 287 |
| CTG CTA GTA TTC GGC CTG ACT GCC AAC AGT GAC ACC CAT CTG CTG CAT<br>Leu Leu Val Phe Gly Leu Thr Ala Asn Ser Asp Thr His Leu Leu His<br>                  100                105              110 | 335 |
| GGC CAG TCC CTG ACA CTG TCC ACC TGC GGC CTG AGA CAG TAC AGC CAG<br>Gly Gln Ser Leu Thr Leu Ser Thr Cys Gly Leu Arg Gln Tyr Ser Gln<br>                115                120              125 | 383 |
| CCT CAG TTT CGC ATC AAA GGA GGG CTC TTC GCC GAC ATC GCC TCC CAC<br>Pro Gln Phe Arg Ile Lys Gly Gly Leu Phe Ala Asp Ile Ala Ser His<br>        130                135              140 | 431 |
| CCC TGG CAG GCT GCC ATC TTT GCC AAG CAC AGG AGG TCG CCC GGA GAG<br>Pro Trp Gln Ala Ala Ile Phe Ala Lys His Arg Arg Ser Pro Gly Glu<br>        145                150              155 | 479 |
| CGG TTC CTG TGC GGG GGC ATA CTC ATC AGC TCC TGC TGG ATT CTC TCT<br>Arg Phe Leu Cys Gly Gly Ile Leu Ile Ser Ser Cys Trp Ile Leu Ser<br>160                  165                170              175 | 527 |
| GCC GCC CAC TGC TTC CAG GAG AGG TTT CCG CCC CAC CAC CTG ACG GTG<br>Ala Ala His Cys Phe Gln Glu Arg Phe Pro Pro His His Leu Thr Val<br>                180                185              190 | 575 |
| ATC TTG GGC AGA ACA TAC CGG GTG GTC CCT GGC GAG GAG GAG CAG AAA<br>Ile Leu Gly Arg Thr Tyr Arg Val Val Pro Gly Glu Glu Glu Gln Lys<br>            195                200              205 | 623 |
| TTT GAA GTC GAA AAA TAC ATT GTC CAT AAG GAA TTC GAT GAT GAC ACT<br>Phe Glu Val Glu Lys Tyr Ile Val His Lys Glu Phe Asp Asp Asp Thr<br>        210                215              220 | 671 |
| TAC GAC AAT GAC ATT GCG CTG CTG CAG CTG AAA TCG GAT TCG TCC CGC<br>Tyr Asp Asn Asp Ile Ala Leu Leu Gln Leu Lys Ser Asp Ser Ser Arg<br>225                  230                235 | 719 |
| TGT GCC CAG GAG AGC AGC GTG GTC CGC ACT GTG TGC CTT CCC CCG GCG<br>Cys Ala Gln Glu Ser Ser Val Val Arg Thr Val Cys Leu Pro Pro Ala<br>240                  245              250              255 | 767 |
| GAC CTG CAG CTG CCG GAC TGG ACG GAG TGT GAG CTC TCC GGC TAC GGC<br>Asp Leu Gln Leu Pro Asp Trp Thr Glu Cys Glu Leu Ser Gly Tyr Gly<br>                260                265              270 | 815 |
| AAG CAT GAG GCC TTG TCT CCT TTC TAT TCG GAG CGG CTG AAG GAG GCT<br>Lys His Glu Ala Leu Ser Pro Phe Tyr Ser Glu Arg Leu Lys Glu Ala<br>            275                280              285 | 863 |
| CAT GTC AGA CTG TAC CCA TCC AGC CGC TGC ACA TCA CAA CAT TTA CTT<br>His Val Arg Leu Tyr Pro Ser Ser Arg Cys Thr Ser Gln His Leu Leu<br>        290                295              300 | 911 |
| AAC AGA ACA GTC ACC GAC AAC ATG CTG TGT GCT GGA GAC ACT CGG AGC<br>Asn Arg Thr Val Thr Asp Asn Met Leu Cys Ala Gly Asp Thr Arg Ser<br>305                  310                315 | 959 |
| GGC GGG CCC CAG GCA AAC TTG CAC GAC GCC TGC CAG GGC GAT TCG GGA | 1007 |

```
Gly Gly Pro Gln Ala Asn Leu His Asp Ala Cys Gln Gly Asp Ser Gly
320                 325                 330                 335

GGC CCC CTG GTG TGT CTG AAC GAT GGC CGC ATG ACT TTG GTG GGC ATC      1055
Gly Pro Leu Val Cys Leu Asn Asp Gly Arg Met Thr Leu Val Gly Ile
                340                 345                 350

ATC AGC TGG GGC CTG GGC TGT GGA CAG AAG GAT GTC CCG GGT GTG TAC      1103
Ile Ser Trp Gly Leu Gly Cys Gly Gln Lys Asp Val Pro Gly Val Tyr
                355                 360                 365

ACA AAG GTT ACC AAC TAC CTA GAC TGG ATT CGT GAC AAC ATG CGA CCG      1151
Thr Lys Val Thr Asn Tyr Leu Asp Trp Ile Arg Asp Asn Met Arg Pro
                370                 375                 380

TGATAGGGAT CC                                                         1163
```

(2) INFORMATION FOR SEQ ID NO:6:

(i) SEQUENCE CHARACTERISTICS:
        (A) LENGTH: 383 amino acids
        (B) TYPE: amino acid
        (D) TOPOLOGY: linear (ii) MOLECULE TYPE: protein (xi) SEQUENCE DESCRIPTION: SEQ ID NO:6:

```
Met Lys Lys Val Val Leu Gly Lys Lys Gly Asp Thr Val Glu Leu Thr
 1               5                  10                  15

Cys Thr Ala Ser Gln Lys Lys Ser Ile Gln Phe His Trp Lys Asn Ser
                20                  25                  30

Asn Gln Ile Lys Ile Leu Gly Asn Gln Gly Ser Phe Leu Thr Lys Gly
            35                  40                  45

Pro Ser Lys Leu Asn Asp Arg Ala Asp Ser Arg Arg Ser Leu Trp Asp
        50                  55                  60

Gln Gly Asn Phe Pro Leu Ile Ile Lys Asn Leu Lys Ile Glu Asp Ser
 65                  70                  75                  80

Asp Thr Tyr Ile Cys Glu Val Glu Asp Gln Lys Glu Glu Val Gln Leu
                 85                  90                  95

Leu Val Phe Gly Leu Thr Ala Asn Ser Asp Thr His Leu Leu His Gly
                100                 105                 110

Gln Ser Leu Thr Leu Ser Thr Cys Gly Leu Arg Gln Tyr Ser Gln Pro
            115                 120                 125

Gln Phe Arg Ile Lys Gly Gly Leu Phe Ala Asp Ile Ala Ser His Pro
        130                 135                 140

Trp Gln Ala Ala Ile Phe Ala Lys His Arg Arg Ser Pro Gly Glu Arg
145                 150                 155                 160

Phe Leu Cys Gly Gly Ile Leu Ile Ser Ser Cys Trp Ile Leu Ser Ala
                165                 170                 175

Ala His Cys Phe Gln Glu Arg Phe Pro Pro His His Leu Thr Val Ile
                180                 185                 190

Leu Gly Arg Thr Tyr Arg Val Val Pro Gly Glu Glu Glu Gln Lys Phe
            195                 200                 205

Glu Val Glu Lys Tyr Ile Val His Lys Glu Phe Asp Asp Asp Thr Tyr
        210                 215                 220

Asp Asn Asp Ile Ala Leu Leu Gln Leu Lys Ser Asp Ser Ser Arg Cys
225                 230                 235                 240

Ala Gln Glu Ser Ser Val Val Arg Thr Val Cys Leu Pro Pro Ala Asp
                245                 250                 255

Leu Gln Leu Pro Asp Trp Thr Glu Cys Glu Leu Ser Gly Tyr Gly Lys
            260                 265                 270
```

```
His Glu Ala Leu Ser Pro Phe Tyr Ser Glu Arg Leu Lys Glu Ala His
            275                 280                 285

Val Arg Leu Tyr Pro Ser Ser Arg Cys Thr Ser Gln His Leu Leu Asn
        290                 295                 300

Arg Thr Val Thr Asp Asn Met Leu Cys Ala Gly Asp Thr Arg Ser Gly
305                 310                 315                 320

Gly Pro Gln Ala Asn Leu His Asp Ala Cys Gln Gly Asp Ser Gly Gly
                325                 330                 335

Pro Leu Val Cys Leu Asn Asp Gly Arg Met Thr Leu Val Gly Ile Ile
            340                 345                 350

Ser Trp Gly Leu Gly Cys Gly Gln Lys Asp Val Pro Gly Val Tyr Thr
        355                 360                 365

Lys Val Thr Asn Tyr Leu Asp Trp Ile Arg Asp Asn Met Arg Pro
370                 375                 380
```

(2) INFORMATION FOR SEQ ID NO:7:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:7:

```
ATGCATGGCC AGTCCCTGAC ACTGACCATG GGTAAGCTTA TTGTGGACGG CTCGGAT        57
```

(2) INFORMATION FOR SEQ ID NO:8:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:8:

```
GTCGACCTAC TCTCCAAACT GATCAATG        28
```

(2) INFORMATION FOR SEQ ID NO:9:

(i) SEQUENCE CHARACTERISTICS:
        (A) LENGTH: 1139 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 3..1133

(xi) SEQUENCE DESCRIPTION: SEQ ID NO:9:

```
TC ATG AAG AAA GTA GTA CTT GGC AAG AAA GGC GAT ACA GTG GAG CTC        47
   Met Lys Lys Val Val Leu Gly Lys Lys Gly Asp Thr Val Glu Leu
    1               5                  10                  15

ACG TGC ACA GCT AGC CAG AAG AAG AGC ATT CAA TTC CAC TGG AAG AAC        95
Thr Cys Thr Ala Ser Gln Lys Lys Ser Ile Gln Phe His Trp Lys Asn
                20                  25                  30

TCC AAC CAG ATT AAG ATC CTT GGT AAC CAA GGT AGC TTC TTA ACT AAG       143
Ser Asn Gln Ile Lys Ile Leu Gly Asn Gln Gly Ser Phe Leu Thr Lys
            35                  40                  45
```

-continued

| | | | | | | | | | | | | | | | | |
|---|---|---|---|---|---|---|---|---|---|---|---|---|---|---|---|---|
| GGC | CCA | TCC | AAG | CTT | AAC | GAT | CGC | GCT | GAC | TCT | CGT | CGT | AGC | CTT | TGG | 191 |
| Gly | Pro | Ser | Lys | Leu | Asn | Asp | Arg | Ala | Asp | Ser | Arg | Arg | Ser | Leu | Trp | |
| | | 50 | | | | 55 | | | | | 60 | | | | | |
| GAC | CAA | GGT | AAC | TTT | CCA | CTG | ATC | ATC | AAG | AAT | CTT | AAG | ATC | GAA | GAC | 239 |
| Asp | Gln | Gly | Asn | Phe | Pro | Leu | Ile | Ile | Lys | Asn | Leu | Lys | Ile | Glu | Asp | |
| | 65 | | | | | 70 | | | | | 75 | | | | | |
| TCT | GAT | ACG | TAT | ATC | TGT | GAA | GTA | GAG | GAT | CAG | AAA | GAG | GAA | GTT | CAA | 287 |
| Ser | Asp | Thr | Tyr | Ile | Cys | Glu | Val | Glu | Asp | Gln | Lys | Glu | Glu | Val | Gln | |
| 80 | | | | | 85 | | | | | 90 | | | | | 95 | |
| CTG | CTA | GTA | TTC | GGC | CTG | ACT | GCC | AAC | AGT | GAC | ACC | CAT | CTG | CTG | CAT | 335 |
| Leu | Leu | Val | Phe | Gly | Leu | Thr | Ala | Asn | Ser | Asp | Thr | His | Leu | Leu | His | |
| | | | | 100 | | | | | 105 | | | | | 110 | | |
| GGC | CAG | TCC | CTG | ACA | CTG | ATT | GTG | GAG | GGC | TCG | GAT | GCA | GAG | ATC | GGC | 383 |
| Gly | Gln | Ser | Leu | Thr | Leu | Ile | Val | Glu | Gly | Ser | Asp | Ala | Glu | Ile | Gly | |
| | | | 115 | | | | | 120 | | | | | 125 | | | |
| ATG | TCA | CCT | TGG | CAG | GTG | ATG | CTT | TTC | CGG | AAG | AGT | CCC | CAG | GAG | CTG | 431 |
| Met | Ser | Pro | Trp | Gln | Val | Met | Leu | Phe | Arg | Lys | Ser | Pro | Gln | Glu | Leu | |
| | | | 130 | | | | | 135 | | | | | 140 | | | |
| CTG | TGT | GGG | GCC | AGC | CTC | ATC | AGT | GAC | CGC | TGG | GTC | CTC | ACC | GCC | GCC | 479 |
| Leu | Cys | Gly | Ala | Ser | Leu | Ile | Ser | Asp | Arg | Trp | Val | Leu | Thr | Ala | Ala | |
| | | 145 | | | | | 150 | | | | | 155 | | | | |
| CAC | TGC | CTC | CTG | TAC | CCG | CCC | TGG | GAC | AAG | AAC | TTC | ACC | GAG | AAT | GAC | 527 |
| His | Cys | Leu | Leu | Tyr | Pro | Pro | Trp | Asp | Lys | Asn | Phe | Thr | Glu | Asn | Asp | |
| 160 | | | | | 165 | | | | | 170 | | | | | 175 | |
| CTT | CTG | GTG | CGC | ATT | GGC | AAG | CAC | TCC | CGC | ACC | AGG | TAC | GAG | CGA | AAC | 575 |
| Leu | Leu | Val | Arg | Ile | Gly | Lys | His | Ser | Arg | Thr | Arg | Tyr | Glu | Arg | Asn | |
| | | | | 180 | | | | | 185 | | | | | 190 | | |
| ATT | GAA | AAG | ATA | TCC | ATG | TTG | GAA | AAG | ATC | TAC | ATC | CAC | CCC | AGG | TAC | 623 |
| Ile | Glu | Lys | Ile | Ser | Met | Leu | Glu | Lys | Ile | Tyr | Ile | His | Pro | Arg | Tyr | |
| | | | | 195 | | | | | 200 | | | | | 205 | | |
| AAC | TGG | CGG | GAG | AAC | CTG | GAC | CGG | GAC | ATT | GCC | CTG | ATG | AAG | CTG | AAG | 671 |
| Asn | Trp | Arg | Glu | Asn | Leu | Asp | Arg | Asp | Ile | Ala | Leu | Met | Lys | Leu | Lys | |
| | | | 210 | | | | | 215 | | | | | 220 | | | |
| AAG | CCT | GTT | GCC | TTC | AGT | GAC | TAC | ATT | CAC | CCT | GTG | TGT | CTG | CCC | GAC | 719 |
| Lys | Pro | Val | Ala | Phe | Ser | Asp | Tyr | Ile | His | Pro | Val | Cys | Leu | Pro | Asp | |
| | | 225 | | | | | 230 | | | | | 235 | | | | |
| AGG | GAG | ACG | GCA | GCC | AGC | TTG | CTC | CAG | GCT | GGA | TAC | AAG | GGG | CGG | GTG | 767 |
| Arg | Glu | Thr | Ala | Ala | Ser | Leu | Leu | Gln | Ala | Gly | Tyr | Lys | Gly | Arg | Val | |
| 240 | | | | | 245 | | | | | 250 | | | | | 255 | |
| ACA | GGC | TGG | GGC | AAC | CTG | AAG | GAG | ACG | TGG | ACA | GCC | AAC | GTT | GGT | AAG | 815 |
| Thr | Gly | Trp | Gly | Asn | Leu | Lys | Glu | Thr | Trp | Thr | Ala | Asn | Val | Gly | Lys | |
| | | | | 260 | | | | | 265 | | | | | 270 | | |
| GGG | CAG | CCC | AGT | GTC | CTG | CAG | GTG | GTG | AAC | CTG | CCC | ATT | GTG | GAG | CGG | 863 |
| Gly | Gln | Pro | Ser | Val | Leu | Gln | Val | Val | Asn | Leu | Pro | Ile | Val | Glu | Arg | |
| | | | 275 | | | | | 280 | | | | | 285 | | | |
| CCG | GTC | TGC | AAG | GAC | TCC | ACC | CGG | ATC | CGC | ATC | ACT | GAC | AAC | ATG | TTC | 911 |
| Pro | Val | Cys | Lys | Asp | Ser | Thr | Arg | Ile | Arg | Ile | Thr | Asp | Asn | Met | Phe | |
| | | 290 | | | | | 295 | | | | | 300 | | | | |
| TGT | GCT | GGT | TAC | AAG | CCT | GAT | GAA | GGG | AAA | CGA | GGG | GAT | GCC | TGT | GAA | 959 |
| Cys | Ala | Gly | Tyr | Lys | Pro | Asp | Glu | Gly | Lys | Arg | Gly | Asp | Ala | Cys | Glu | |
| | 305 | | | | | 310 | | | | | 315 | | | | | |
| GGT | GAC | AGT | GGG | GGA | CCC | TTT | GTC | ATG | AAG | AGC | CCC | TTT | AAC | AAC | CGC | 1007 |
| Gly | Asp | Ser | Gly | Gly | Pro | Phe | Val | Met | Lys | Ser | Pro | Phe | Asn | Asn | Arg | |
| 320 | | | | | 325 | | | | | 330 | | | | | 335 | |
| TGG | TAT | CAA | ATG | GGC | ATC | GTC | TCA | TGG | GGT | GAA | GGC | TGT | GAC | CGG | GAT | 1055 |
| Trp | Tyr | Gln | Met | Gly | Ile | Val | Ser | Trp | Gly | Glu | Gly | Cys | Asp | Arg | Asp | |
| | | | | 340 | | | | | 345 | | | | | 350 | | |
| GGG | AAA | TAT | GGC | TTC | TAC | ACA | CAT | GTG | TTC | CGC | CTG | AAG | AAG | TGG | ATA | 1103 |
| Gly | Lys | Tyr | Gly | Phe | Tyr | Thr | His | Val | Phe | Arg | Leu | Lys | Lys | Trp | Ile | |
| | | | 355 | | | | | 360 | | | | | 365 | | | |

```
CAG AAG GTC ATT GAT CAG TTT GGA GAG TAGGTCGAC                              1139
Gln Lys Val Ile Asp Gln Phe Gly Glu
        370                 375
```

(2) INFORMATION FOR SEQ ID NO:10:

(i) SEQUENCE CHARACTERISTICS:
        (A) LENGTH: 376 amino acids
        (B) TYPE: amino acid
        (D) TOPOLOGY: linear (ii) MOLECULE TYPE: protein (xi) SEQUENCE DESCRIPTION: SEQ ID NO:10:

```
Met Lys Lys Val Val Leu Gly Lys Gly Asp Thr Val Glu Leu Thr
 1               5                  10                  15

Cys Thr Ala Ser Gln Lys Lys Ser Ile Gln Phe His Trp Lys Asn Ser
            20                  25                  30

Asn Gln Ile Lys Ile Leu Gly Asn Gln Gly Ser Phe Leu Thr Lys Gly
                35                  40                  45

Pro Ser Lys Leu Asn Asp Arg Ala Asp Ser Arg Arg Ser Leu Trp Asp
        50                  55                  60

Gln Gly Asn Phe Pro Leu Ile Ile Lys Asn Leu Lys Ile Glu Asp Ser
 65                 70                  75                  80

Asp Thr Tyr Ile Cys Glu Val Glu Asp Gln Lys Glu Glu Val Gln Leu
                85                  90                  95

Leu Val Phe Gly Leu Thr Ala Asn Ser Asp Thr His Leu Leu His Gly
                100                 105                 110

Gln Ser Leu Thr Leu Ile Val Glu Gly Ser Asp Ala Glu Ile Gly Met
            115                 120                 125

Ser Pro Trp Gln Val Met Leu Phe Arg Lys Ser Pro Gln Glu Leu Leu
130                 135                 140

Cys Gly Ala Ser Leu Ile Ser Asp Arg Trp Val Leu Thr Ala Ala His
145                 150                 155                 160

Cys Leu Leu Tyr Pro Pro Trp Asp Lys Asn Phe Thr Glu Asn Asp Leu
                165                 170                 175

Leu Val Arg Ile Gly Lys His Ser Arg Thr Arg Tyr Glu Arg Asn Ile
                180                 185                 190

Glu Lys Ile Ser Met Leu Glu Lys Ile Tyr Ile His Pro Arg Tyr Asn
            195                 200                 205

Trp Arg Glu Asn Leu Asp Arg Asp Ile Ala Leu Met Lys Leu Lys Lys
210                 215                 220

Pro Val Ala Phe Ser Asp Tyr Ile His Pro Val Cys Leu Pro Asp Arg
225                 230                 235                 240

Glu Thr Ala Ala Ser Leu Leu Gln Ala Gly Tyr Lys Gly Arg Val Thr
                245                 250                 255

Gly Trp Gly Asn Leu Lys Glu Thr Trp Thr Ala Asn Val Gly Lys Gly
                260                 265                 270

Gln Pro Ser Val Leu Gln Val Val Asn Leu Pro Ile Val Glu Arg Pro
            275                 280                 285

Val Cys Lys Asp Ser Thr Arg Ile Arg Ile Thr Asp Asn Met Phe Cys
290                 295                 300

Ala Gly Tyr Lys Pro Asp Glu Gly Lys Arg Gly Asp Ala Cys Glu Gly
305                 310                 315                 320

Asp Ser Gly Gly Pro Phe Val Met Lys Ser Pro Phe Asn Asn Arg Trp
                325                 330                 335

Tyr Gln Met Gly Ile Val Ser Trp Gly Glu Gly Cys Asp Arg Asp Gly
```

|     | 340 |     |     | 345 |     |     | 350 |     |
|-----|-----|-----|-----|-----|-----|-----|-----|-----|

Lys Tyr Gly Phe Tyr Thr His Val Phe Arg Leu Lys Lys Trp Ile Gln
                355                 360                 365

Lys Val Ile Asp Gln Phe Gly Glu
    370                 375

(2) INFORMATION FOR SEQ ID NO:11:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:11:

AATTCATGAA GAAAGTAGTA CTTGGCAAGA AA                                    32

(2) INFORMATION FOR SEQ ID NO:12:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:12:

GGCGATACAG TGGAGCTCAC GTGCACAGCT AGCCAGAAGA AGAGCATT                48

(2) INFORMATION FOR SEQ ID NO:13:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:13:

CAATTCCACT GGAAGAACTC CAACCAGATT AAGATCCTTG GTAACCAA                48

(2) INFORMATION FOR SEQ ID NO:14:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:14:

GGTAGCTTCT TAACTAAGGG CCCATCCAAG CTTAACGATC GCGCTGAC                48

(2) INFORMATION FOR SEQ ID NO:15:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:15:

TCTCGTCGTA GCCTTTGGGA CCAAGGTAAC TTTCCAACTG ATCATCAAG                49

(2) INFORMATION FOR SEQ ID NO:16:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:16:

AATCTTAAGA TCGAAGACTC TGATACGTAT ATCTGTGAAG TAGAGGAT               48

(2) INFORMATION FOR SEQ ID NO:17:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:17:

CAGAAAGAGG AAGTTCAACT GCTAGTATTC GGCCTGACTG CCAACAGT               48

(2) INFORMATION FOR SEQ ID NO:18:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:18:

GACACCCATC TGCTGCAGGG CTAATAG                                       27

(2) INFORMATION FOR SEQ ID NO:19:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:19:

GATCCTATTA GCCCTGCAG                                                19

(2) INFORMATION FOR SEQ ID NO:20:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:20:

CAGATGGGTG TCACTGTTGG CAGTCAGGCC GAATACTAGC AGTTGAAC               48

(2) INFORMATION FOR SEQ ID NO:21:

(i) SEQUENCE CHARACTERISTICS:
    (A) LENGTH: 48 base pairs
    (B) TYPE: nucleic acid
    (C) STRANDEDNESS: single
    (D) TOPOLOGY: linear (ii) MOLECULE TYPE: other nucleic acid (xi) SEQUENCE DESCRIPTION: SEQ ID NO:21:

TTCCTCTTTC TGATCCTCTA CTTCACAGAT ATACGTATCA GAGTCTTC                48

(2) INFORMATION FOR SEQ ID NO:22:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:22:

GATCTTAAGA TTCTTGATGA TCAGTGGAAA GTTACCTTGG TCCCAAAG                48

(2) INFORMATION FOR SEQ ID NO:23:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:23:

GCTACGACGA GAGTCAGCGC GATCGTTAAG CTTGGATGGG CCCTTAGT                48

(2) INFORMATION FOR SEQ ID NO:24:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:24:

ATAAGAAGCT ACCTTGGTTA CCAAGGATCT TAATCTGGTT GGAGTTCTT               49

(2) INFORMATION FOR SEQ ID NO:25:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:25:

CCAGTGGAAT TGAATGCTCT TCTTCTGGCT AGCTGTGCAC GTGAGCTC                48

(2) INFORMATION FOR SEQ ID NO:26:

(i) SEQUENCE CHARACTERISTICS:
        (A) LENGTH: 40 base pairs
        (B) TYPE: nucleic acid
        (C) STRANDEDNESS: single -continued (D) TOPOLOGY: linear (ii) MOLECULE TYPE: other nucleic acid (xi) SEQUENCE DESCRIPTION: SEQ ID NO:26:

CACTGTATCG CCTTTCTTGC CAAGTACTAC TTTCTTCATG                                    40